(12) United States Patent
Novak et al.

(10) Patent No.: US 12,097,215 B2
(45) Date of Patent: *Sep. 24, 2024

(54) ANTIBACTERIAL COMPOSITION AND ITS USE IN TREATING BACTERIAL INFECTIONS

(71) Applicant: Vector Vitale IP LLC, North Miami Beach, FL (US)

(72) Inventors: Peter Y. Novak, Sunny Isles Beach, FL (US); Maxim V. Temnikov, Miami, FL (US); Oleksandr Balakin, Dnepropetrovsk (UA)

(73) Assignee: Vector Vitale IP LLC, North Miami Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/100,225

(22) Filed: Jan. 23, 2023

(65) Prior Publication Data

US 2023/0218665 A1 Jul. 13, 2023

Related U.S. Application Data

(60) Continuation of application No. 16/210,790, filed on Dec. 5, 2018, now Pat. No. 11,638,721, which is a division of application No. 15/486,026, filed on Apr. 12, 2017, now Pat. No. 10,183,041.

(51) Int. Cl.
| | | |
|---|---|---|
| *A61K 33/30* | (2006.01) | |
| *A61K 8/19* | (2006.01) | |
| *A61K 9/00* | (2006.01) | |
| *A61K 9/06* | (2006.01) | |
| *A61K 33/24* | (2019.01) | |

(52) U.S. Cl.
CPC ............... *A61K 33/30* (2013.01); *A61K 8/19* (2013.01); *A61K 9/0053* (2013.01); *A61K 9/06* (2013.01); *A61K 33/24* (2013.01)

(58) Field of Classification Search
CPC ........ A61K 33/24; A61K 33/26; A61K 33/30; A23L 33/165
See application file for complete search history.

(56) References Cited

U.S. PATENT DOCUMENTS

| | | |
|---|---|---|
| 4,068,122 A | 1/1978 | Schmidt et al. |
| 5,912,178 A | 6/1999 | Porter et al. |
| 6,451,341 B1 | 9/2002 | Slaga et al. |
| 6,656,127 B1 | 12/2003 | Ben-oren et al. |
| 6,838,020 B2 | 1/2005 | Kelsey et al. |
| 7,473,892 B2 | 1/2009 | Sano et al. |
| 8,512,258 B2 | 8/2013 | Ben Oren et al. |
| 8,512,676 B1 | 8/2013 | Eghbalnia et al. |
| 8,753,889 B1 | 6/2014 | Roeder |
| 9,518,972 B2 | 12/2016 | Joseph et al. |
| 9,861,659 B2 | 1/2018 | Novak et al. |
| 2003/0068351 A1 | 4/2003 | Roig |
| 2003/0118713 A1 | 6/2003 | Bjorkstrom et al. |
| 2004/0013732 A1 | 1/2004 | Farber et al. |
| 2004/0129112 A1 | 7/2004 | Gills et al. |
| 2004/0234450 A1 | 11/2004 | Howes |
| 2007/0207191 A1 | 9/2007 | Kanzer et al. |
| 2009/0042304 A1 | 2/2009 | Anderson et al. |
| 2009/0246143 A1* | 10/2009 | Bonitatibus, Jr. ...... B82Y 15/00 428/404 |
| 2010/0183736 A1 | 7/2010 | Hays |
| 2010/0240089 A1 | 9/2010 | Inskip et al. |
| 2012/0021526 A1 | 1/2012 | Baer et al. |
| 2013/0115650 A1 | 5/2013 | Anbar et al. |
| 2014/0033795 A1 | 2/2014 | Guggenheim et al. |
| 2014/0051116 A1 | 2/2014 | Tea et al. |
| 2014/0219961 A1 | 8/2014 | Jung et al. |
| 2014/0286862 A1 | 9/2014 | Strand et al. |
| 2015/0056297 A1 | 2/2015 | Liu |

(Continued)

FOREIGN PATENT DOCUMENTS

| | | |
|---|---|---|
| CN | 106854147 A | 6/2017 |
| GB | 2531207 A | 4/2016 |

(Continued)

OTHER PUBLICATIONS

Campro Scientific: Metal Isotopes , 2010, 40 pages.*
Albarede, "Medical applications of the Cu, Zn, and S Isotope effects," Metallomics, Jul. 25, 2016, pp. 1056-1070.
CRC Handbook of Chemistry and Physics (49th ed. 1968), pp. 1-3.
Web archived entry dated (Jul. 2, 2014) for iron isotopes ISOFLEX webpage (online), retrieved on (Dec. 10, 2021) from URL https://web.archive.org/web/20140702171618/http://www.isoflex.com/iron.
Jefferson Lab: "It's Elemental", Zinc isotopes, Science Education, May 2017, pp. 1-3.
Web archived entry dated (Jul. 2, 2014) for copper isotopes ISOFLEX webpage (online), retrieved on (Dec. 10, 2021) from URL https://web.archive.org/web/20140702170635/https://www.isoflex.com/copper-cu.

(Continued)

*Primary Examiner* — Kyle A Purdy

(74) *Attorney, Agent, or Firm* — Liang & Hennessey LLP; Stanley D. Liang

(57) ABSTRACT

An antibacterial composition that comprises as active compound at least one light isotope of an element selected from the group which consists of $^{1}H$, $^{12}C$, $^{16}O$, $^{14}N$, $^{39}K$, $^{24}Mg$, $^{64}Zn$, $^{85}Rb$, $^{28}Si$, $^{54}Fe$, $^{92}Mo$, $^{74}Se$, $^{58}Ni$, $^{70}Ge$, $^{52}Cr$, $^{63}Cu$, $^{50}V$, or combinations thereof, wherein the composition is enriched for the at least one light isotope. A method of treating and preventing bacterial diseases in humans and non-human animals by administering the composition. The use of the said composition in human and veterinary medicine for the prevention and treatment of diseases in humans and non-human animals and also as an antiseptic and disinfectant.

4 Claims, 10 Drawing Sheets

(56) References Cited

U.S. PATENT DOCUMENTS

| | | | |
|---|---|---|---|
| 2016/0151415 | A1 | 6/2016 | Novak et al. |
| 2016/0153957 | A1 | 6/2016 | Novak et al. |
| 2018/0055879 | A1 | 3/2018 | Novak et al. |

FOREIGN PATENT DOCUMENTS

| | | |
|---|---|---|
| JP | S57156329 A | 9/1982 |
| JP | S6163619 A | 4/1986 |
| JP | 2005023029 A | 1/2005 |
| RU | 2498807 C1 | 11/2013 |
| UA | 83809 U | 9/2013 |
| WO | 0182871 A2 | 11/2001 |
| WO | 2006072054 A1 | 7/2006 |
| WO | 2010068130 | 6/2010 |

OTHER PUBLICATIONS

Web archived entry dated (Jan. 4, 2016) for chrominum isotopes ISOFLEX webpage (online), retrieved on (Jul. 15, 2021) from URL https://web.archive.org/web/20160104070825/https://isoflex.com/chromium-cr.

Lemire et al., "Antimicrobial Activity of Metals: Mechanisms, Molecular Targets and Applications," Nature Reviews Microbiology 11.6 (2013) pp. 371-384.

Web archived entry dated (Feb. 17, 2015) for nickel isotopes ISOFLEX webpage (online), retrieved on (Sep. 15, 2020) from URL https://web.archive.org/web/20150217090943/https://isoflex.com/nickel-ni.

U.S. Appl. No. 15/486,026, filed Apr. 12, 2017, Office Action dated Apr. 17, 2018.

U.S. Appl. No. 15/486,026 Notice of Allowance dated Sep. 18, 2018 incl. Examiners Amendment.

Zhu et al., "Mass Fractionation Processes of Transition Metal Isotopes," Earth and Planetary Science Letters 200.1-2 (2002), pp. 47-62.

Johnson et al., "Correction of Instrumentally Produced Mass Fractionation During Isotopic Analysis of Fe by Thermal Ionization Mass Spectrometry," International Journal of Mass Spectrometry 193.1 (1999), pp. 87-99.

Porcheron et al., "Iron, Copper, Zinc, and Manganese Transport and Regulation in Pathogenic Enterobacteria," Frontiers in Cell and Infection Microbiol. vol. 3, article 90, (Dec. 5, 2013).

James et al., How (beta)-Lactam Antibiotics Enter Bacteria: a Dialogue with the Porins, PLOS ONE, 4(5): e5453 (May 12, 2009).

Bornet et al., "Omp35, a New, Enterobacter Aerogenes Porin Involved in Selective Susceptbility to Cephalosporins," Antimicrobial Agents and Chemotherpy, Jun. 2004, pp. 2153-2158.

Ghai et al., "Exploring Bacterial Outer Membrane Barrier to Combat Bad Bugs," Infection and Drug Resistance 2017:, 10, pp. 261-273 (Aug. 30, 2017).

Hobman et al., "Bacterial Antimicrobial Metal ion Resistance," Journal of Medical Microbiology 64:, pp. 471-497 (2014).

Fosset et al., "A Non-radioactive Method for Measuring Cu uptake in HepG2 cells," Journal of Inorganic Biochemistry 99.5 (2005), pp. 1018-1022.

Iqbal et al., "Antibacterial Activity of Copper-Amino Acid Complexes," J. Pak. Med. Assoc 40.9 (1990), pp. 221-222.

Anacona et al., "Synthesis and Antibacterial Activity of Ceftriazone Metal Complexes," Transition Metal Chemistry 30.7, (2005), pp. 897-901.

Duncan et al., "Treatment of Primary Isolated Shoulder Sepsis in the Adult Patient," Clinical Orthopaedics and Related Research 466.6, (2008, pp. 1392-1396.

Navarrete et al., "Copper Isotope Fractionation During Surface Adsorption and Intracellular Incorporation by Bacteria," Geochimica et Cosmochimica acta 75.3 (2011), pp. 784-799.

Institute for Reference Materials and Measurements: Certificate (Zinc Isotopes) (2007).

Florez et al., Isotope Ratio Mapping by Means of Laser Ablation-Single Collector-ICP-Mass Spectrometry: Zn Tracer Studies in thin Sections of Daphnia Magna, J. Anal., At. Spectrom, 28: 1005 (2013).

Yoshida, "Learning of Zinc Oxide in Acidic Solution," Materials Trans, 44. pp. 2489-2493, (2003).

U.S. Appl. No. 15/486,026 Interview Summary & Refs dated Sep. 18, 2018.

U.S. Appl. No. 15/486,026 Terminal Disclaimer & Approval dated Sep. 7, 2018.

\* cited by examiner

Figure 1
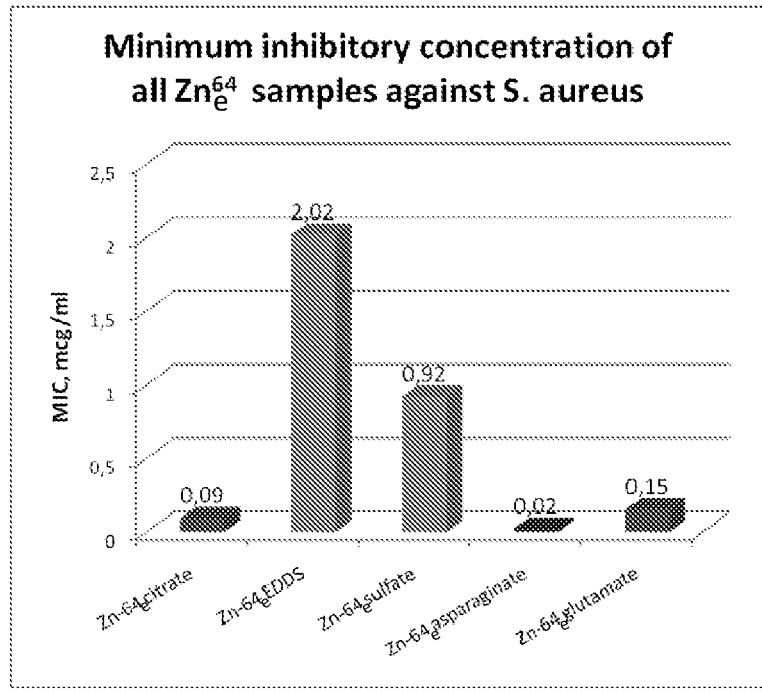
Fig. 1a
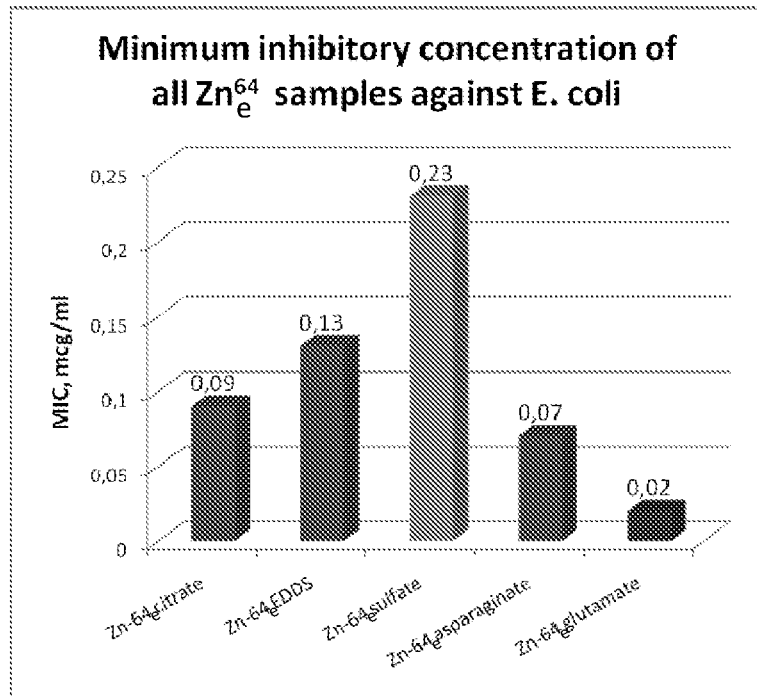
Fig. 1b

FIGURE 2
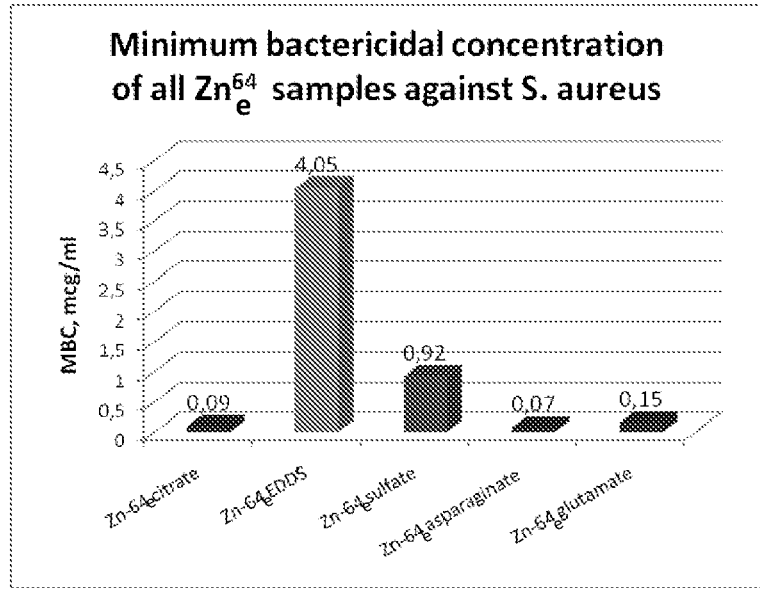
Fig. 2a
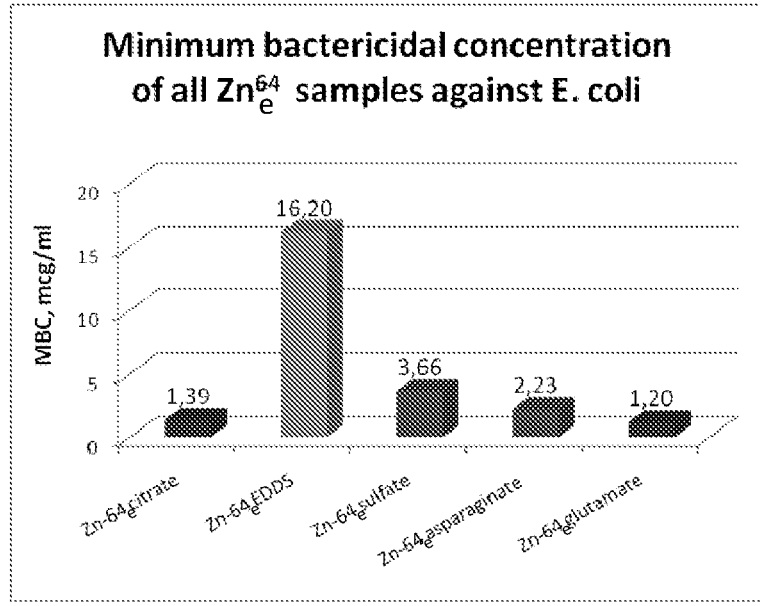
Fig. 2b

FIGURE 3
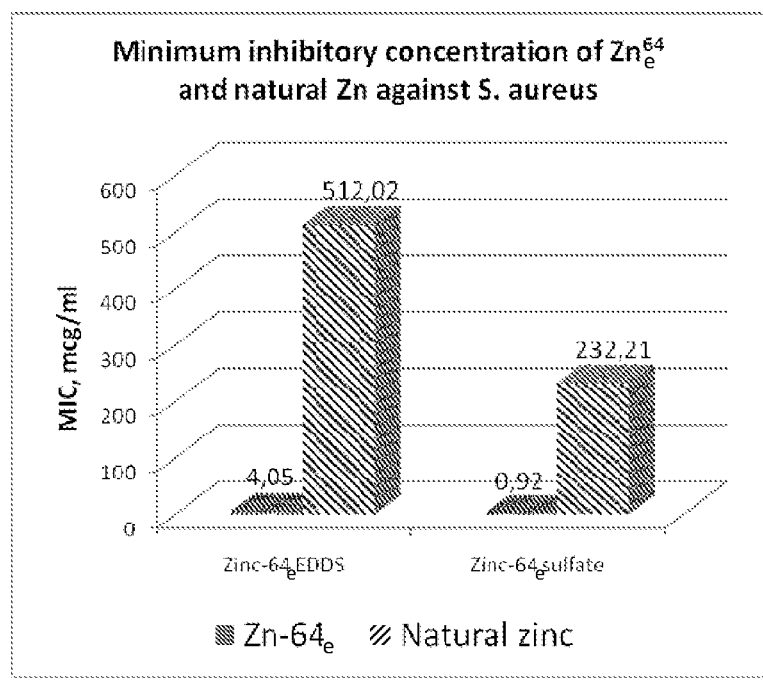
Fig. 3a
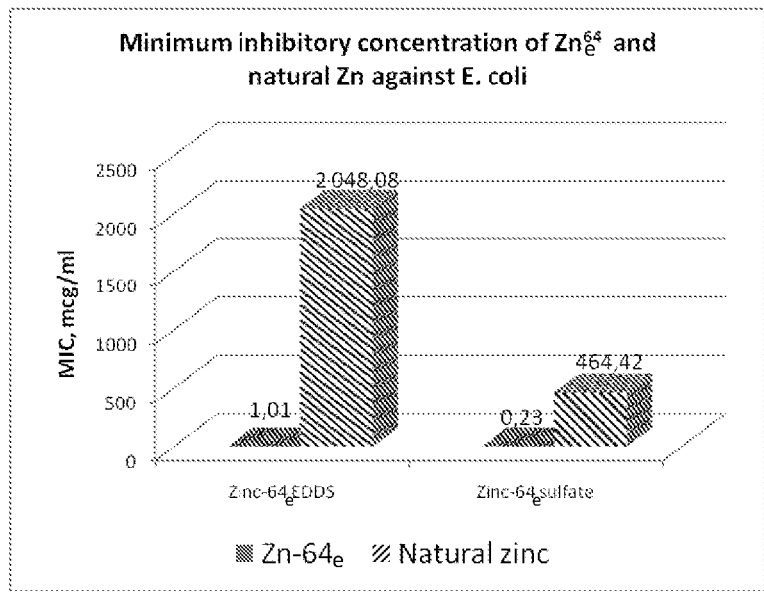
Fig. 3b

FIGURE 5
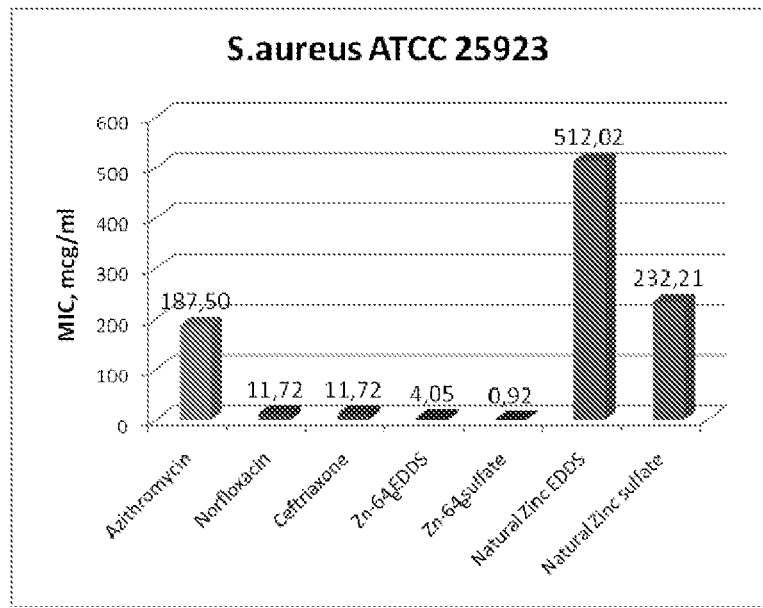
Fig. 5a
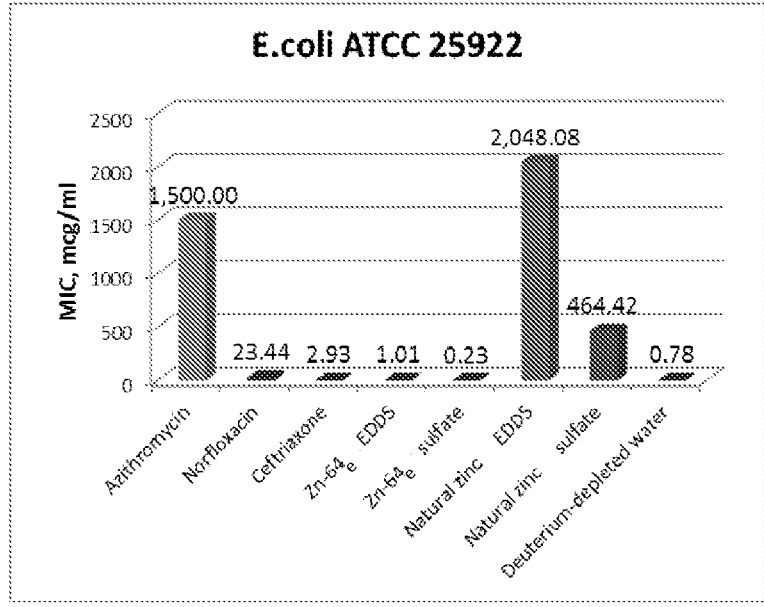
Fig. 5b

ANTIBACTERIAL COMPOSITION AND ITS USE IN TREATING BACTERIAL INFECTIONS

CROSS-REFERENCE TO RELATED APPLICATION

This application claims the benefit of and is a continuation of U.S. patent application Ser. No. 15/486,026, filed on Apr. 12, 2017 and published on Oct. 18, 2018 as U.S. 2018/0296596, entitled "Antibacterial Composition and Its Use in Treating Bacterial Infections," the entire contents of which are hereby incorporated by reference herein.

FIELD OF THE INVENTION

The present invention relates to a novel antibacterial composition that is enriched for one or more light isotopes of one or more chemical elements as an active ingredient and the use of such a composition in the treatment and prevention of bacterial infections in humans and non-human animals.

BACKGROUND OF THE INVENTION

The variability of isotopes is known as the isotope effect, a term describing the mass-dependent variations of natural isotope contents for a particular element. The isotope effect is a consequence of the Heisenberg uncertainty principle on 75 levels of the energy distribution of molecular vibrations (Metallomics, 2016, Accepted Manuscript DOI: 10.1039/C6MT00148C). It is known that the isotopic weight has an effect on the value of the effective radius of electron orbits of atoms and leads to changes in the characteristics of the fine structure of atomic energy levels. Biochemical processes of organisms are highly dependent on the conditions of their occurrence, usually using resonant effects, so the slightest deformations of electron orbitals can lead to disruption of biochemical reactions.

A number of studies have demonstrated that the isotopic composition of tissues and organs can serve as a diagnostic marker. In particular, the study of correlations of Cu and Zn isotopes in blood showed their promising relationship to age, sex and pathologies. For example, assessment of the ratio of Cu isotopes in the blood serum is a new approach to the diagnosis and prognosis of liver cirrhosis (see M. Costas-Rodriguez et al., *Isotopic analysis of Cu in blood serum by multi-collector ICP-mass spectrometry: a new approach for the diagnosis and prognosis of liver cirrhosis?* Metallomics 7: 491-498 (2015)), and the isotopic composition of Zn in breast tissue makes it possible to diagnose cancer (F. Lamer et al., *Zinc isotopic compositions of breast cancer tissue*, Metallomics 7: 107-112 (2015)).

In particular, it was found that natural water and most foods that are used by humans contain heavy isotopes of chemical elements. Every human, being a complex biochemical system, fractionates heavy isotopes during his lifetime. As a result, heavy isotopes, which accumulate in the human organism starting at birth, gradually "integrate" into the cells.

While not wishing to be bound by theory, the present inventors believe that each of hydrogen, carbon, oxygen, nitrogen potassium, magnesium, zinc, rubidium, silicon, iron, molybdenum, selenium, nickel, germanium, chromium, copper, and vanadium play important roles in autocatalytic reactions in the body of an animal, such as a human or other mammal. The products of such autocatalytic reactions, such as proteins, play important chemical and structural roles in the body, including immune function. Fully functional products of such reactions require a specific, "correct" chirality at various chiral centers within the product. The inventors further understand that heavy isotopes accumulate in the body beginning at birth such that, over time, the relative abundance of each element's isotopes drifts further and further from the naturally occurring relative abundance, becoming increasingly over-weighted with respect to heavy isotopes. Heavy isotopes can affect autocatalytic reactions by reducing the proportion of products that have the "correct" chirality. See, e.g., Tsuneomi Kawasaki et al., *Asymmetric Autocatalysis Triggered by Carbon Isotope ($^{13}C/^{12}C$) Chirality*, Science 324: 492-95 (2009). This causes a reduction in the proportion of products of autocatalytic reactions that are fully functional. In sum, the cumulative divergence of the body's isotope relative abundances from the natural relative abundance causes a decrease in the functionality of various proteins and other molecules in the body, leading to a decline in health with age.

The present inventors believe such a decline can be countered by restoring the body's original isotope relative abundances, or by moving the isotope relative abundances in that direction. Similarly, pathogenic infectious bacteria can be suppressed by treating them with light isotopes of the elements listed above, which can alter the chirality of the autocatalytic products of such bacteria, resulting in their death or suppressed growth. Thus, treatment with light isotopes can have the dual result of improving the body's ability to fight off a bacterial infection and simultaneously killing or suppressing the growth of infective bacteria. Further, the quantity of light isotope that is effective may be proportional to the quantity of the corresponding element that is present in the body. Where the body contains a relatively large quantity of the element, a correspondingly relatively large amount of the element's light isotope will be required to provide an effective dosage amount. On the other hand, where the body contains a relatively small quantity of the element, a correspondingly relatively small amount of the element's light isotope will be required to provide an effective dosage amount.

Light isotopes have been used in medicine, veterinary medicine, food industry and agriculture without producing adverse effects on organisms.

Patent RU2498807 purports to disclose a new treatment of acute radiation sickness which uses water with light isotopes as a therapeutic agent. The remedy is said to improve survival and accelerate recovery of hematopoiesis and body weight.

International publication no. WO 01/82871 describes a method of diagnosis and treatment of colon cancer. This method uses zinc and the unstable isotope $^{62}Zn$ in the form of zinc acetate, zinc chloride and zinc sulfate, as well as the phosphate carrier.

According to U.S. publication no. 2016/0151415, a pharmaceutical composition for improving health condition and treatment of pathologies and degenerative diseases includes a pharmaceutically acceptable carrier and an active isotope selective ingredient that includes at least one chemical element wherein the isotope distribution is different from that occurring in nature, inherent in such chemical element. Thus $^{39}K$, $^{24}Mg$, $^{64}Zn$, $^{85}Rb$, $^{26}Si$, $^{40}Ca$, $^{63}Cu$, $^{54}Fe$, $^{52}Cr$, $^{58}Ni$, $^{92}Mo$, $^{107}Ag$, $^{79}Br$, $^{35}Cl$ and combinations thereof are used as possible selective isotopes. However, the antibacterial effect of the above isotopes is not described in the said application.

Publication No. GB2531207 purports to disclose an antibacterial agent which consists of at least one of the isotopes of hydrogen selected from the group including $^1H$, $^2H$, $^3H$, $^4H$, $^5H$, $^6H$ and $^7H$, a hydrogen molecule (H2), metal hydride, a hydrogen ion (H$^+$), a hydride ion (H$^-$) and atomic hydrogen. The composition described in this publication is said to exhibit antibacterial activity and reduce propagation of drug-resistant microorganisms. In addition, hydrogen, after its exposure to pathogenic microorganisms, combines with oxygen to form water. According to the publication, this eliminates adverse effects of the antibacterial agent on the organism to which it is administered, and the said agent has little effect on the host organism even if it is administered in combination with another drug(s).

There remains a need for new, effective antibacterial compositions.

SUMMARY OF THE INVENTION

In one embodiment, the invention provides an antibacterial composition that comprises as an antibacterial agent at least one light isotope selected from the group consisting of $^1H$, $^{12}C$, $^{16}O$, $^{14}N$, $^{39}K$, $^{24}Mg$, $^{64}Zn$, $^{85}Rb$, $^{28}Si$, $^{54}Fe$, $^{92}Mo$, $^{74}Se$, $^{58}Ni$, $^{70}Ge$, $^{52}Cr$, $^{63}Cu$, and $^{50}V$, either in elemental form or in the form of a pharmaceutically acceptable salt, compound, or complex, wherein the composition is enriched for the at least one light isotope relative to the natural abundance of the isotope. The at least one light isotope that the composition is enriched for preferably is present in a bacteriostatic or bactericidal effective amount. In preferred embodiments, the composition is suitable for various routes of administration, such as topical or oral administration. In certain embodiments, the composition further comprises at least one additional ingredient suitable to the form of the composition, including carriers and excipients such as diluents, solvents (such as water), binders, lubricants, coloring agents, and preservatives, which are conventional and known to the person of ordinary skill in the art. The composition preferably is formulated for a specific route of administration such as, but not limited to, injection (e.g. intravenous, intraperitoneal, or subcutaneous injection), topical administration and oral administration. Specific exemplary forms of the composition include a topical solution, spray, lotion, salve, ointment, gel, cream, soap, shampoo, patch, powder and foam, and an oral tablet, capsule, syrup, suspension, lozenge, gum, spray, and solution, and a solution or other composition suitable for intravenous, intraperitoneal, subcutaneous, or other route of administration by injection. Oral compositions of the invention may be formulated for immediate, delayed, or sustained release and may also formulated for enteric release. Topical compositions of the invention preferably include at least one absorption-enhancing agent such as DMSO. In a preferred embodiment, the at least one light isotope that the composition is enriched for comprises $^{64}Zn$. In such an embodiment, the $^{64}Zn$ preferably constitutes between about 90% and about 99.9% of the zinc in the composition. In alternative embodiments, any of the above antibacterial compositions can comprise as an antibacterial agent at least one light isotope selected from any subgroup selected from the group consisting of $^1H$, $^{12}C$, $^{16}O$, $^{14}N$, $^{39}K$, $^{24}Mg$, $^{64}Zn$, $^{85}Rb$, $^{28}Si$, $^{54}Fe$, $^{92}Mo$, $^{74}Se$, $^{58}Ni$, $^{70}Ge$, $^{52}Cr$, $^{63}Cu$, and $^{50}V$, either in elemental form or in the form of a pharmaceutically acceptable salt, compound, or complex, wherein the composition is enriched for the at least one light isotope relative to the natural abundance of the isotope.

In various embodiments, the light isotope in the composition of the invention is present in elemental form or in the form of one or more of an oxide, sulfate, citrate, gluconate, chelate, or other compound, or in any other pharmaceutically acceptable form. The at least one light isotope may be present in the composition in the form of a salt with a pharmaceutically acceptable inorganic or organic acid. Exemplary salts of the light isotope include sulfate, glutamate, asparaginate, aspartate, citrate, and ethylene diamine disuccinic acid (referred to in this application both as "EDDA" and as "EDDS") salts. An exemplary oxide is deuterium-depleted water.

In an embodiment, the composition of the invention further comprises an additional antibacterial agent or other active ingredient. In an embodiment, the composition of the invention comprises an agent that enhances the stability of the composition.

The light isotope may constitute between about 0.1% and about 99% of the composition by weight. When the light isotope is present in the form of a salt, the anionic portion of the salt acts as a carrier. When water is part of the said composition, it may function as a carrier and diluent.

The antibacterial composition, in accordance with the invention, can be used in human or veterinary medicine to treat infections in humans and non-human animals, including veterinary mammals, caused by bacterial pathogens.

The invention also provides a method of preparing a composition of the invention, such as a composition for administration orally, topically, or by injection, such as the compositions listed above, which comprises combining a compound, complex, or pharmaceutically acceptable salt enriched for at least one of the above-listed isotopes with at least one excipient. The invention also provides a method of preparing a composition of the invention which comprises incorporating an effective amount of a compound, complex, or pharmaceutically acceptable salt enriched for at least one of the above-listed isotopes into a composition for administration to a human or veterinary animal, such as a veterinary mammal, such as a composition for administration orally, topically, or by injection, such as the compositions listed above. In one embodiment, the method comprises combining a prepared topical formulation or liquid oral formulation, such as an ointment, cream, lotion, gel, salve, spray, or solution, with an effective amount of a compound, complex, or pharmaceutically acceptable salt enriched for at least one of the above-listed isotopes to provide a composition of the invention.

The invention also provides a method of treating conditions characterized by bacterial infection or growth, such as bacterial infections, in humans and veterinary animals, such as non-human mammals, comprising administering to a human or veterinary animal, e.g. a veterinary mammal, in need of such treatment (e.g. one that exhibits such a condition) an effective therapeutic amount of the composition of the invention. The invention also provides a method of preventing bacterial infections, and conditions characterized by bacterial infection or growth, in humans and veterinary animals (such as veterinary mammals) in need of such treatment, such as humans and veterinary animals (such as veterinary mammals) known to be susceptible to, prone to or highly susceptible to such infections or conditions, comprising administering to a human or veterinary animal (such as a veterinary mammal) in need of such treatment an effective prophylactic amount of the composition of the invention. In preferred embodiments of such methods, the composition comprises a bacteriostatic or bactericidal effective amount of $^{64}Zn_e$ (zinc that is enriched for zinc-64), present as an element or in the form of a pharmaceutically acceptable salt, compound or complex thereof. In particularly preferred embodiments, $^{64}$Zn constitutes between about 90% and about 99.9% of the $^{64}$Zn$_e$.

The composition of the invention can also be used as a disinfectant of surfaces and as an antibacterial component in compositions used in agriculture. The invention thus also provides a method of disinfecting surfaces comprising administering an effective amount of the composition to the surface to be disinfected. In these aspects, the composition of the invention may advantageously be in the form of a sprayable liquid or powder or a spreadable liquid or powder. The composition may be provided in concentrated form for later dilution with an appropriate vehicle or carrier prior to use.

In another embodiment, the invention provides a composition for use in the treatment or prevention of a bacterial infection, or of a condition characterized by bacterial infection or growth, wherein the composition comprises as an antibacterial agent at least one light isotope selected from the group consisting of $^1$H, $^{12}$C, $^{16}$O, $^{14}$N, $^{39}$K, $^{24}$Mg, $^{64}$Mn, $^{85}$Rb, $^{28}$Si, $^{54}$Fe, $^{92}$Mo, $^{74}$Se, $^{58}$Ni, $^{70}$Ge, $^{52}$Cr, $^{63}$Cu, and $^{50}$V, either in elemental form or in the form of a pharmaceutically acceptable salt, compound, or complex, wherein the composition is enriched for the at least one light isotope relative to the natural abundance of the isotope. The composition is as described in the preceding paragraphs. In a preferred embodiment, the at least one light isotope that the composition is enriched for is $^{64}$Zn$_e$. More preferably, in such a composition, $^{64}$Zn constitutes between about 90% and about 99.9% of the $^{64}$Zn$_e$. For example, $^{64}$Zn may constitute at least about 95% of the $^{64}$Zn$_e$ or at least about 99% of the $^{64}$Zn$_e$, such as about 99% or 99.9% of the $^{64}$Zn$_e$.

The technical problem that is solved by the use of this invention consists in the development of an antibacterial composition which, on the one hand, has high bacteriostatic and bactericidal activities and, on the other hand, does not cause any toxic effects associated with the use of antibiotic active compounds and also does not cause the development of resistant microorganisms.

BRIEF DESCRIPTION OF THE DRAWINGS

The advantages of the present invention will be readily appreciated as the same becomes better understood by reference to the following detailed description when considered in connection with the accompanying drawings wherein.

DETAILED DESCRIPTION OF THE INVENTION

Figure 1C:
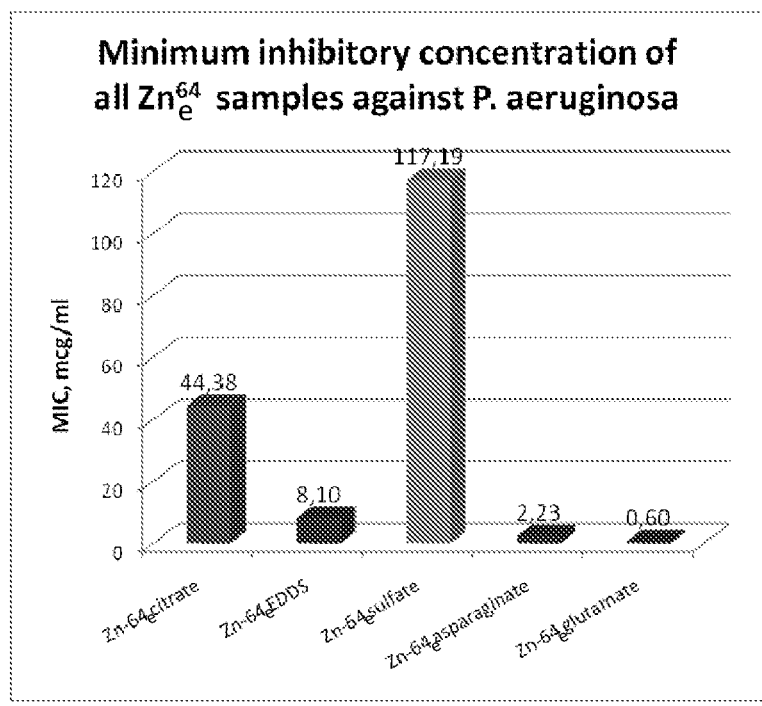
FIG. 1 presents diagrams (FIGS. 1a-1c) that compare the MICs of antibacterial compositions that contain zinc enriched for $^{64}$Zn in the form of different salts: $^{64}$Zn$_e$ citrate, $^{64}$Zn$_e$ EDDA, $^{64}$Zn$_e$ sulfate, $^{64}$Zn$_e$ aspartate, $^{64}$Zn$_e$ glutamate.

Definitions of the terms used in this application are given hereinafter to ensure their unambiguous understanding by specialists. Furthermore, unless otherwise specifically stated, all scientific and technical terms used herein have the same meaning as commonly understood by a person of ordinary skill in the art.

The term "isotope", as used herein, refers to a variant of a particular chemical element which are rather similar in their physical and chemical properties but have a different atomic mass. According to the proton-neutron model developed by D. I. Ivanenko and W. Heisenberg (1932), atoms of all chemical elements consist of three types of elementary particles: positively charged protons, negatively charged electrons, and neutrons that have no charge. The number of protons p in the nucleus determines the atomic number Z of the chemical element in Mendeleev's periodic table. The proton and the neutron, which have a common name—nucleons—have almost identical weight. The mass of the neutron (1.00866 amu) is somewhat greater than the proton mass (1.00727 amu). The electron mass is much smaller than that of the nucleons (for example, the proton-to-electron mass ratio is 1836.13). Therefore, the mass of the atom is concentrated in its nucleus. Hence, the mass number of the atom A is connected with the atomic number by a simple relation A=p+n=Z+n, where n is the number of neutrons in the nucleus of an atom. The number of protons in the nucleus of an atom uniquely determines the position of an element in the periodic table of the elements. Furthermore, the number of protons determines the number of electrons present in a neutral atom thus determining the chemical properties of this atom. However, atoms with the same atomic number Z (and hence the number of protons p) may have different neutron numbers n. Thus atoms with different atomic mass numbers may occupy the same position on the periodic table. Chemical elements having the same atomic number but a different atomic mass are known as isotopes.

As used herein, the term "light isotopes" refers to the following isotopes: $^1$H $^{12}$C, $^{16}$O, $^{14}$N, $^{39}$K, $^{24}$Mg, $^{64}$Zn, $^{85}$Rb, $^{28}$Si, $^{54}$Fe, $^{92}$Mo, $^{74}$Se, $^{58}$Ni, $^{70}$Ge, $^{52}$Cr, $^{63}$Cu, and $^{50}$V.

The "natural abundance" of an isotope refers to the fraction of the total amount of the corresponding element that the isotope represents, on a mole-fraction basis (that is, not, for example, on a mass basis). For example, if $^{64}$Zn had an earth natural abundance of 48.63%, that would mean that 48.63% of Zn atoms on earth are the isotope $^{64}$Zn. When a composition is "enriched" for a certain isotope, the abundance of the isotope in the composition is greater than the isotope's natural abundance. For the preceding $^{64}$Zn example, a composition in which $^{64}$Zn constitutes more than 48.63% of the total Zn in the composition, on a mole-fraction basis, would be "enriched" for $^{64}$Zn. Throughout this application, a subscript "e" following a light isotope chemical symbol or element name indicates that the designated element is enriched for that isotope. For example, $^{64}$Zn refers to the light isotope zinc-64, whereas $^{64}$Zn$_e$ refers to zinc that is enriched for zinc-64. Thus, "$^{64}Zn_e$ aspartate," for example, refers to zinc aspartate in which the zinc is enriched for zinc-64.

The proportion of an element that is present as a particular isotope of the element is often expressed relative to a ratio called the standard isotope ratio or SIR. The abundance of the isotope of interest is the numerator of the SIR and the abundance of the most abundant isotope is the denominator. For example, $^{12}C$ is the most abundant carbon isotope and $^{13}C$ is a second carbon isotope. Assuming a standard abundance value for C-12 of 98.89% and a standard abundance value for $^{13}C$ of 1.11%, the SIR for $^{13}C$ would be 1.11/98.89=0.01122. Each SIR is obtained from a reference material. Deviations from the SIR may be observed in non-reference materials.

For ease and convenience, the abundance of a heavy isotope in a material of interest may be expressed relative to the heavy isotope's "standard" abundance in the reference material by reference to the difference in isotope ratios, expressed in parts per thousand or "‰" and referred to as delta-[isotope] or δ-[X], where "[X]" represents the isotope of interest. The δ value is calculated as $((R_{sample}-SIR)/SIR) \times 1000‰$, equivalent to $((R_{sample}/SIR)-1) \times 1000‰$, where $R_{sample}$ is the isotope ratio of the sample under evaluation. For example, if the carbon standard contains 99% $^{12}C$ and 1% $^{13}C$, and the sample has 98.95% $^{12}C$ and 1.05% $^{13}C$, then the corresponding SIR, or $^{13}C/^{12}C$ of the standard, is 1/99, or 0.0101, and the $^{13}C/^{12}C$ of the sample is 1.05/98.95, or 0.0106, so $\delta^{13}C_{sample}=((0.0106/0.0101)-1) \times 1000‰=49.5‰$ (also known as 49.5 permil) or 0.0495.

Relative abundance of an isotope can also be expressed with respect to different isotopes' absolute abundances expressed in terms of "atom percent" and "fractional abundance." Atom percent is calculated as ($^AX$/(sum of all X isotopes))×100, whereas fractional abundance is simply $^AX$/(sum of all X isotopes), where "$^AX$" is a measure of the quantity of isotope A of element X in a sample, and "sum of all X isotopes" is a measure of the total quantity of element X in a sample. Enrichment for a specific isotope in a sample of interest may be expressed as a percentage of the fractional abundance or atom percent of a reference standard. For example, if a reference standard contained potassium, of which 93.3% was $^{39}K$, then the atom percent of $^{39}K$ would be 93.3% and its fractional abundance would be 0.933. If a sample were to contain potassium, of which 95.0% was $^{39}K$, then the sample would be enriched with respect to $^{39}K$ by (95.0−93.3)/93.3=1.82%. If a sample were said to be enriched with respect to $^{39}K$ by 5% relative to the standard, then the percentage of the potassium in the sample that is $^{39}K$ would be 1.05×93.3=97.97%.

The degree of enrichment of a certain isotope also may be expressed with respect to the difference D(I) (where "I" represents the identity of the isotope) between 100% and the isotope's natural abundance, expressed as a mole percentage of the total amount of the corresponding element. For example, if $^{64}Zn$ had a natural abundance of 48.63%, then D($^{64}Zn$)=100%−48.63%=51.37%. A sample's enrichment may then be expressed as the amount by which D is reduced. For the $^{64}Zn$ example, for a sample in which D($^{64}Zn$) is reduced by 10%, D($^{64}Zn$) would equal 51.37% minus (10%×51.37), which equals 46.233%, and the $^{64}Zn$ atom percent in the sample would be (100%−46.233%), which equals 53.767%. The sample would thus be characterized as enriched for $^{64}Zn$ by 10% of D.

The authors of the present invention have discovered that a composition that comprises at least one light isotope selected from the group consisting of $^1H$, $^{12}C$, $^{16}O$, $^{14}N$, $^{39}K$, $^{24}Mg$, $^{64}Zn$, $^{85}Rb$, $^{28}Si$, $^{54}Fe$, $^{92}Mo$, $^{74}Se$, $^{58}Ni$, $^{70}Ge$, $^{52}Cr$, $^{63}Cu$, and $^{49}V$, wherein the composition is enriched for the at least one light isotope relative to the natural abundance of the isotope, has pronounced bacteriostatic and bactericidal effects approximately equal to or greater than those provided by conventional antibiotics. Thus, the antibacterial compositions of the present invention inhibit the growth of and/or kill bacteria. In addition to being enriched for a light isotope as described above, the composition may comprise one or more additional active ingredients, as well as water and inert auxiliary ingredients such as carriers, diluents and the like which are used to formulate the said composition and may be pharmaceutically acceptable or pharmaceutically unacceptable (which are used as intermediates in the preparation of pharmaceutically acceptable agents). The ability of a chemical element enriched for a light isotope to exhibit antibacterial activity was revealed by the authors of the present invention and has not been described previously in the literature.

As used herein, the terms "treat," "treating," "treatment of" a condition encompass performing an act (such as administering the composition of the invention) in order to cure, eradicate, or diminish the severity of, the condition treated. These terms thus encompass accomplishing any one or more of curing, eradicating, and diminishing the severity of the condition treated. As used herein, the terms "prevent," "preventing," "prevention of" a condition encompass performing an act (such as administering the composition of the invention) in order to prevent the occurrence of the condition and diminish the severity of the condition if it occurs subsequent to the act. These terms thus encompass accomplishing any one or more of wholly preventing the condition from occurring and diminishing the severity of the condition if it occurs subsequent to the act.

For reference with respect to the invention, the above-listed isotopes are considered to have the natural abundances, on a mole-fraction basis, shown in the following table. The table also shows the corresponding percentages preferred for use in the compositions of the invention, on a mole-fraction basis (lower limits are provided; in every case, the maximum theoretical upper limit is 100%). For example, in a composition of the invention that uses a therapeutic amount of $^{64}Zn$, the zinc in the composition preferably would contain at least about 90% $^{64}Zn$. Compositions that contain isotopes with lower levels of enrichment may also be effective and are within the scope of the invention.

| Isotope | Natural abundance (%) | % for therapeutic use |
| --- | --- | --- |
| $^1H$ | 99.9885 | at least 99.99% |
| $^{12}C$ | 98.93 | at least 99.9% |
| $^{14}N$ | 99.632 | at least 99.9% |
| $^{16}O$ | 99.757 | at least 99.9% |
| $^{24}Mg$ | 78.99 | at least about 95%* |
| $^{28}Si$ | 92.2297 | at least about 95% |
| $^{39}K$ | 93.2581 | at least about 98% |
| $^{50}V$ | 0.250 | at least about 35% |
| $^{52}Cr$ | 83.789 | at least about 90% |
| $^{54}Fe$ | 5.845 | at least about 80%* |
| $^{58}Ni$ | 68.0769 | at least about 90%* |
| $^{63}Cu$ | 69.17 | at least about 90%* |
| $^{64}Zn$ | 48.63 | at least about 90%* |
| $^{70}Ge$ | 20.84 | at least about 80%* |
| $^{74}Se$ | 0.89 | at least about 50%* |

-continued

| Isotope | Natural abundance (%) | % for therapeutic use |
|---|---|---|
| $^{85}$Rb | 72.17 | at least about 90%* |
| $^{92}$Mo | 14.84 | at least about 80%* |

*In some embodiments, an enrichment level about 10 percentage points lower may be used for this isotope for therapeutic application and preferably for prophylactic use. For example, for $^{64}$Zn, a composition in which the zinc contains at least about 80% $^{64}$Zn may be administered for therapeutic or prophylactic purposes such as preventing bacterial infection of a wound or cut.

The term "minimum inhibitory concentration," or "MIC," as used herein, represents the lowest concentration of a test drug that prevents growth of a test culture. The minimum inhibitory concentration of a bacteriostatic or bactericidal agent is that which causes complete suppression of visible growth of a given microorganism in media under standard test conditions. It is expressed in micrograms ("mcg")/ml or in units of activity.

The term "minimum bactericidal concentration," or "MBC," as used herein, represents the lowest concentration of a test drug that causes a bactericidal effect, i.e. the concentration that results in the death of a bacterium test strain, such as a standard bacterium test strain. It may be expressed, for example, in mg/1 or mcg/ml.

In an antibacterial composition of the invention, the composition is enriched for at least one light isotope selected from the group that includes $^{1}$H, $^{12}$C, $^{16}$O, $^{14}$N, $^{39}$K, $^{24}$Mg, $^{85}$Rb, $^{28}$Si, $^{54}$Fe, $^{92}$Mo, $^{74}$Se, $^{58}$Ni, $^{70}$Ge, $^{52}$Cr, $^{63}$Cu, $^{50}$V or any combination thereof. At least one light isotope may be present as a component of a chemical compound, such as the salt of an organic or inorganic acid, which is pharmaceutically acceptable and can be administered to humans and veterinary animals (such as veterinary mammals). Exemplary salts include the chloride, citrate, sulfate, aspartate, glutamate, asparaginate and ethylene diamine disuccinic acid (referred to herein interchangeably as "EDDS" and "EDDA") salts of the light isotope, and hydrates of such salts. For example, zinc enriched for $^{64}$Zn may be present in the form of the salt zinc aspartate or the salt zinc asparaginate.

The antibacterial composition of the invention may be prepared by making a compound that is enriched for a light isotope, such as the salt of an organic or inorganic acid and the light isotope, purifying the obtained compound by standard methods, and subsequent preparation of the claimed antibacterial composition in any appropriate form, such as an aqueous solution. Such methods are well known and the person of ordinary skill in the art can prepare a compound containing a light isotope of a particular chemical element, its salt in particular. The preparation process of the complex of aspartic acid and zinc which is enriched for the isotope $^{64}$Zn is described in the Examples below. The light isotope-enriched compound may be administered as a component or ingredient of any convenient dosage form. Such dosage forms include topical dosage forms such as solutions, sprays, lotions, salves, ointments, gels, creams, soaps, shampoos, and foams, oral dosage forms such as tablets, capsules, syrups, suspensions, lozenges, gums, sprays, patches, and solutions, and conventional dosage forms suitable for other conventional routes of administration. Conventional dosage forms are well-known to the person of ordinary skill in the art. Examples of such dosage forms and their preparation are described in, for example, Loyd V. Allen, Jr. et al., *Ansel's Pharmaceutical Dosage Forms and Drug Delivery Systems* (8th ed. 2005) (Lippincott Williams & Wilkins), and publications cited therein.

The antibacterial composition of the invention may contain water as solvent. The antibacterial composition of the invention may be in the form of an aqueous solution to be administered by any suitable route, such as orally and topically, or in the form of a gel, salve, ointment, paste, cream, foam, lotion, drops, or other topical composition. The composition may further include any suitable excipient known to the person of ordinary skill in the art, including solvents, binders, lubricants, emulsifiers, detergents, surfactants, buffers, stabilizers, and preservatives. These are described in commonly used references, such as the Handbook of Pharmaceutical Excipients.

The concentration of the light isotope-enriched element in a composition of the invention, relative to the total weight of the composition, varies according to conventional composition weights and the dosage of the light isotope-enriched element. Appropriate dosages of the light isotope-enriched element are set forth below. Preferably the composition of the invention comprises an effective amount of at least one light isotope, wherein "effective amount" refers to that amount that either suppresses, partially or completely, the growth of bacteria at the affected site, or kills some or all of the bacteria at the affected site. As stated above, the quantity of light isotope that is effective is proportional to the quantity of the corresponding element that is present in the body. Where the body contains a relatively large quantity of the element, a correspondingly relatively large amount of the element's light isotope will be required to provide an effective dosage amount. On the other hand, where the body contains a relatively small quantity of the element, a correspondingly relatively small amount of the element's light isotope will be required to provide an effective dosage amount. These quantities are reflected in the "guidance amounts" for each element, the recommended amount for daily human consumption, as detailed below.

In certain embodiments, the preferred dosage of any of the light isotopes is proportional to various authoritative daily ingestion guidances (e.g. recommended dietary allowance (USRDA), adequate intake (AI), recommended dietary intake (RDI)) of the corresponding element. The light isotope dosage is preferably between about ½ and about 20 times the guidance amount of the corresponding element, more preferably between about 1 and about 10 times the guidance amount, even more preferably between about 1 and about 3 times the guidance amount. Thus, in preferred embodiments, a single dose of a composition of the invention for daily administration would be formulated to comprise a quantity within these ranges, such as about ½, about 1, about 3, about 5, about 10, and about 20 times the guidance amount. These amounts generally are for oral intake or topical application. In some embodiments, the preferred intravenous dosage is lower, such as from about 1/10 to about ½ the guidance amount. In another embodiment, intravenous treatment of sepsis preferably employs a zinc dosage of from about 10 to about 100 times the daily guidance amount. Doses at the low end of these ranges are appropriate for anyone with a heightened sensitivity to a specific element or class of elements (e.g., those with kidney problems). For zinc, the guidance amount ranges from 2 mg in infants to 8-11 mg (depending on sex) for ages 9 and up. Guidance amounts for some of the elements used in the compositions of the invention are presented below based on information obtained from https://ods.od.nih.gov/factsheets/list-all/ and https://health.gov/dietaryguidelines/2015/guidelines/appendix-7/, summarized below. Daily dosages discussed throughout this application may be subdivided into fractional dosages and the fractional dosages administered the appropriate number of times per day to provide the total daily dosage amount (e.g. ½ the daily dose administered twice daily, ⅓ the daily dose administered three times daily, etc.).

| Element/Isotope | guidance amount, daily |
|---|---|
| magnesium/$^{24}$Mg | 30-420 mg |
| | (400-420 mg in males 14+; |
| | 310-360 mg in females 14+) |
| potassium/$^{39}$K | 1 to 3 years: 3 g/day |
| | 4 to 8 years: 3.8 g/day |
| | 9 to 13 years: 4.5 g/day |
| | 14 to 18 years: 4.7 g/day |
| | Age 19 and older: 4.7 g/day |
| chromium/$^{52}$Cr | Hexavalent chromium should be avoided. |
| | Chromium complexes are preferred for oral |
| | administration (e.g. picolinate, |
| | dinicocysteinate, as nicotinic acid complex). |
| | For parenteral administration, chromic chloride |
| | at 4 mcg/ml may be used. |
| | 0-6 mos. 0.2 mcg |
| | 7-12 mos. 5.5 mcg |
| | 1-3 yrs 11 mcg |
| | 4-8 yrs 15 mcg |
| | 9-13 yrs females: 21 mcg, males: 25 mcg |
| | 14-18 yrs females: 24 mcg, males; 35 mcg |
| | 19-50 yrs females: 25 mcg, males: 35 mcg |
| | >50 yrs females: 20 mcg, males: 30 mcg |
| Iron/$^{54}$Fe | Birth to 6 months 0.27 mg |
| | 7-12 months 11 mg |
| | 1-3 years 7 mg |
| | 4-8 years 10 mg |
| | 9-13 years 8 mg |
| | 14-18 years males: 11 mg, females: 15 mg |
| | 19-50 years males: 8 mg, females: 18 mg |
| | Adults 51 years and older 8 mg |
| Copper/$^{63}$Cu | adequate: |
| | 0 to 6 months: 200 mcg |
| | 7 to 12 months: 220 mcg |
| | recommended: |
| | 1 to 3 years: 340 mcg |
| | 4 to 8 years: 440 mcg |
| | 9 to 13 years: 700 mcg |
| | 14 to 18 years: 890 mcg |
| | 19 and older: 900 mcg |
| Zinc/$^{64}$Zn | Birth to 6 months 2 mg |
| | 7 months-3 years 3 mg |
| | Children 4-8 years 5 mg |
| | Children 9-13 years 8 mg |
| | 14-18 years (boys) 11 mg |
| | 14-18 years (girls) 9 mg |
| | Adults (men) 11 mg |
| | Adults (women) 8 mg |
| Selenium/$^{74}$Se | Birth to 6 months 15 mcg |
| | 7 months-3 years 20 mcg |
| | Children 4-8 years 30 mcg |
| | Children 9-13 years 40 mcg |
| | 14 years and older 55 mcg |

For purposes of the invention, for the following substances, the following amounts are considered to be benchmark daily intakes: rubidium: between about 1 and 2 mg per day; "light water" (water enriched for $^{1}$H and thus depleted for deuterium and/or tritium): about 400 micrograms; silicon: about 10 mg; molybdenum: about 1.5 mg; germanium: about 1 mg; nickel: about 100 mcg; vanadium: about 40 mcg. Thus, a composition of the invention that contains light rubidium or light water, for example, preferably contains $^{85}$Rb$_e$ or light water ($^{1}$H$_{e2}$O), respectively, in an amount between about 1 times and about 20 times these amounts, more preferably between about 1 and about 10 times these amounts, and even more preferably between about 1 and about 3 times these amounts.

Based on the above, in certain embodiments, a composition of the invention containing $^{64}$Zn$_e$ as the active ingredient, prepared for administration to a male 19 years of age or older, preferably contains, in a single dose, between about 11 mg and about 220 mg $^{64}$Zn$_e$ (zinc enriched for $^{64}$Zn), more preferably between about 11 mg and about 110 mg $^{64}$Zn$_e$, even more preferably between about 11 mg and about 33 mg $^{64}$Zn$_e$. Such a composition may be, for example, for oral administration, such as a tablet or capsule, or for topical administration, such as a cream, gel, ointment, or lotion (optionally containing DMSO or other absorption-enhancing agent and other appropriate excipients).

In certain preferred embodiments, the daily dosages of $^{64}$Zn$_e$ in a composition of the invention, such as a tablet, capsule, salve, cream, lotion, or ointment, comprise between about 10 and about 50 mg of $^{64}$Zn$_e$, such as about 15 mg, about 30 mg, or about 45 mg of $^{64}$Zn$_e$, which may be elemental or in the form of $^{64}$Zn$_e$ asparaginate, $^{64}$Zn$_e$ aspartate, or another pharmaceutically acceptable $^{64}$Zn$_e$ salt or complex. Such compositions preferably contain, in addition to the $^{64}$Zn$_e$ compound, excipients suitable to the formulation type. In analogous preferred embodiments, the daily dosages of another light isotope may be determined relative to these dosages and the relative guidance amounts of $^{64}$Zn$_e$ and the other light isotope. For example, if the guidance amount of another light isotope were one-half (½) that of zinc, then preferred daily doses of the other light isotope in a composition of the invention would be between about 5 mg and about 25 mg, such as about 7.5 mg, about 15 mg, or about 22.5 mg, in elemental form or as a pharmaceutically acceptable salt or complex.

In some embodiments, a composition of the invention may contain two or more compounds that are each enriched for a light isotope. The percentages and masses above may represent each of the light isotope-enriched compounds and may alternatively represent their total percentage or mass.

The composition of the invention may include an additional antibacterial agent, as well as auxiliary agents which improve the stability and antibacterial properties of the composition and are generally present in many finished pharmaceutical products.

Compositions that contain zinc are known and include topical formulations that contain 20% or 40% w/w zinc oxide and oral formulations such as tablets and capsules that contain 30 mg or 50 mg zinc in various forms. In an embodiment, the present invention provides comparable compositions in which the zinc is enriched for $^{64}$Zn. For example, the zinc in such compositions may contain at least about 90% $^{64}$Zn, such as between about 90% and about 99.9% $^{64}$Zn, such as about 90%, about 95%, about 99%, or about 99.9% $^{64}$Zn, on a mole fraction basis. Examples of such compositions include: a paste that contains between about 20% w/w and about 40% w/w $^{64}$Zn$_e$ oxide, such as about 20%, about 30%, or about 40% w/w $^{64}$Zn$_e$ oxide; an ointment that contains about 20% w/w $^{64}$Zn$_e$ oxide; tablets and capsules that contain between about 30 mg and about 50 mg of $^{64}$Zn$_e$, such as about 30, about 40, or about 50 mg $^{64}$Zn$_e$, present in the form of zinc gluconate, zinc bisglycinate chelate, or any pharmaceutically acceptable zinc salt such as those enumerated above (aspartate, asparaginate, glutamate, EDDA, etc.). Such compositions preferably also contain excipients suitable to each formulation type. Examples of such excipients and representative paste, ointment, tablet and capsule compositions, and their preparation, are disclosed, for example, in *Ansel's Pharmaceutical Dosage Forms and Drug Delivery Systems* (8th ed. 2005) (Lippincott Williams & Wilkins) (capsules and tablets are discussed, for example, at pages 204-75, and ointments and pastes are discussed, for example, at pages 276-97; both sections are incorporated by reference herein in their entirety), and publications cited therein. Dosage amounts of any topical compositions of the invention preferably vary with skin thickness at the site of administration, with higher dosage amounts being used on thicker skin and lower dosages on thinner skin.

The pH of the said composition, when aqueous (including emulsions such as oil-in-water and water-in-oil emulsions), may be between about 2 and about 10, such as between about 2 and about 4, between about 4 and about 6, between about 6 and about 8, or between about 8 and about 10. For example, the composition may have a pH of about 2, about 3, about 4, about 5, about 6, about 7, or about 8, as appropriate for the route of administration and site of administration.

The antibacterial composition enriched for a light isotope as described herein slows, reduces, or stops the growth of bacteria at the targeted site or kills such bacteria, prevents bacterial infection, and/or eliminates bacterial infection wherein the said infection is caused by at least one bacterium. The bacteria or bacterium may be either gram-negative or gram-positive. Examples of infection-causing genera and species that the composition of the invention is effective against include *Bacillus, Escherichia coli, Acinetobacter, Salmonella, Haemophilus influenzae, Vibrio parahaemolyticus, Enterococcus, Pneumococcus, Neisseria, Neisseria gonorrhoeae, Neisseria meningitidis, Staphylococcus aureus, Staphylococcus epidermidis*, Group A *Streptococcus*, Group B *Streptococcus*, Group C/G *Streptococcus, Listeria monocytogenes, Klebsiella pneumoniae, Shigella, Vibrio cholerae, Pseudomonas aeruginosa*.

The invention thus provides a method of treating a condition that has a bacterial component, including those that are caused by or characterized by a bacterial infection or excessive bacterial growth, wherein the method comprises administering a composition of the invention to a person or veterinary animal, such as a veterinary mammal, that exhibits such a condition. In an embodiment of this method of the invention, the bacterial component of the condition comprises one or more gram-positive or gram-negative bacterium, including the bacteria enumerated in the preceding paragraph. In other embodiments of this method of the invention, the condition treated is acne, such as acne vulgaris, or sepsis. The invention also provides a method of preventing a condition that has a bacterial component, including those that are caused by or characterized by a bacterial infection or excessive bacterial growth, wherein the method comprises administering a composition of the invention to a person or veterinary animal, such as a veterinary mammal, who is in need of such treatment. In an embodiment, the method comprises administering the composition of the invention to a site that is likely to become the site of a bacterial infection or excessive bacterial growth, such as an open wound such as a cut, or the site of a surgical incision, or to an area of skin in the vicinity of acne inflammation or where acne inflammation has previously occurred, or to another area prone to infection, in order to kill bacteria and/or prevent bacterial growth at the site of administration. In various embodiments, such administration can be oral, topical or by injection. The compositions of the invention may also be used to treat sepsis, preferably via intravenous administration. In the context of the invention, "excessive bacterial growth" means greater growth than would ordinarily be expected at the site that is intended to be treated by administering the composition. In the context of the invention, "veterinary animal" refers to an animal that a veterinarian would treat, including, but not limited to, pets such as dogs and cats, farm animals such as cows and horses, and zoo animals such as monkeys, chimpanzees, and orangutans, lions, tigers, and elephants.

Thus, the invention provides a method of treating or preventing a condition that has a bacterial component, including those that are caused by or characterized by a bacterial infection or excessive bacterial growth comprising administering an effective amount of the composition to a human patient or veterinary animal, such as a veterinary mammal, in need of such treatment. The composition may be administered topically, orally, or by injection, and is formulated accordingly. The invention further provides compositions for use in the treatment or prevention of a condition that has a bacterial component, including those that are caused by or characterized by a bacterial infection or excessive bacterial growth, wherein the composition is for administration to a human patient or veterinary animal, such as a veterinary mammal, in need of such treatment. Such conditions include those detailed in the preceding paragraph. The composition may be administered topically, orally, or by injection, and is formulated accordingly.

An advantage of the proposed composition is that the antibacterial composition which comprises and is enriched for at least one light isotope selected from the group consisting of $^{1}$H, $^{12}$C, $^{16}$O, $^{14}$N, $^{39}$K, $^{24}$Mg, $^{64}$Zn, $^{85}$Rb, $^{28}$Si, $^{54}$Fe, $^{92}$Mo, $^{74}$Se, $^{58}$Ni, $^{70}$Ge, $^{52}$Cr, $^{63}$Cu, $^{50}$V and any combination thereof, does not cause any toxic effects when administered, unlike many other antibacterial agents. These elements play an important physiological role in many organisms, including humans. Consequently, the composition of the invention provides, in addition to its bactericidal and bacteriostatic activity, a number of additional advantages associated with the optimization of the various biological functions that make use of these elements, including catalytic, structural and regulatory functions.

The present invention will further be more fully disclosed by reference to the following Examples. The Examples are given as illustrations and should not be construed to limit the scope of the invention in any way. The following Examples present data relating to $^{64}$Zn, the light isotope of zinc.

EXAMPLES

Example 1. Preparation Process of $^{64}$Zn$_e$ Aspartate $^{64}$Zn$_e$ aspartate (racemic) having the following formula (in which "$^{64}$Zn$^{2+}$" refers, in this instance, to Zn$^{2+}$ enriched for $^{64}$Zn) was prepared in the experiment.

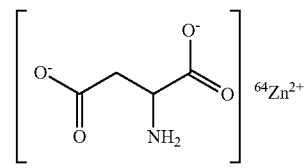

At the first stage, zinc oxide enriched for $^{64}$Zn was prepared using $^{64}$Zn$_e$ sulfate as the starting compound.

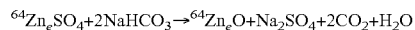

For this purpose, $^{64}$Zn$_e$ sulfate (zinc was at least 99.9% $^{64}$Zn, although $^{64}$Zn$_e$ of lower purity may be effective) in an amount of 0.01 mole) was dissolved in 150 ml of water (T=50-70° C.) wherein 1.68 g (0.02 mole) of sodium bicarbonate was added in small portions, to prevent severe foaming, with constant stirring in a magnetic stirrer. After completion of foaming the solution was stirred for another 30 minutes and then left for 1 hour until a white precipitate was formed. During this process, the temperature was maintained at about 60° C. to prevent crystallization of sodium sulfate. The solution with the precipitate, which precipitate was $^{64}Zn_eO$, was then filtered without cooling. The resulting precipitate—$^{64}Zn_eO$—was washed with warm demineralized water (T=40-50° C.) and dried to constant weight in a desiccator over the dehydrating agent phosphorus pentoxide.

After that, 425 ml of demineralized water was poured into a 1 liter flask and heated under reflux to 80° C. 1.33 g (0.01 mole) of aspartic acid was dissolved in water with stirring by a magnetic stirrer. After aspartic acid was completely dissolved, 0.8 g (0.01 mole) of $^{64}Zn_eO$ obtained at the previous stage was added to the clear solution. The mixture was stirred with heating to 80° C. for 1½-2 hours till complete dissolution of $^{64}Zn_eO$. The reaction formula is shown below:

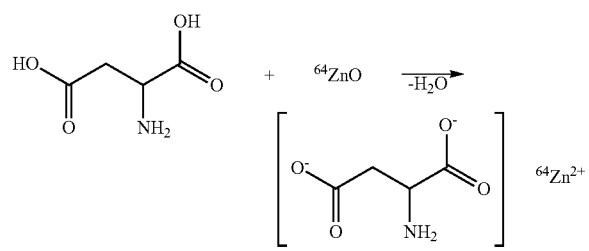

If the precipitate ($^{64}Zn_e$ oxide) was not dissolved completely, the solution was filtered and the undissolved $^{64}Zn_eO$ was collected and dried to its constant weight to determine the $^{64}Zn_e$ complex concentration in the resulting solution. The solution was transferred into a volumetric measure and made up to a volume of 425 ml using demineralized water. 425 ml of $^{64}Zn_e$-aspartic acid complex containing $^{46}Zn_e$ in the amount of approximately 0.0015 g $^{64}Zn_e$ (1.5 mg $^{64}Zn_e$)/ml was thus prepared.

In Examples 2 through 4 that follow, in the $^{64}Zn_e$ compounds that were used in the experiments described, the zinc was about 99.4% $^{64}Zn$ on a mole fraction basis.

Example 2. Determination of MIC and MBC of the Antibacterial Composition Based on Various $^{64}Zn_e$ Compounds The minimum inhibitory concentration (MIC) and minimum bactericidal concentration (MBC) of the antibacterial composition enriched for the light isotope zinc $^{64}Zn_e$ was evaluated in the experiment. Five samples of $^{64}Zn_e$ ($^{64}Zn_e$ citrate, $^{64}Zn_e$ salt with EDDA, $^{64}Zn_e$ sulfate, $^{64}Zn_e$ asparaginate, $^{64}Zn_e$ glutamate) were tested. S. aureus ATCC 25923, E. coli ATCC 25922 and P. aeruginosa ATCC 27853 were used as test cultures.

The studies were carried out using the method of serial dilutions in broth. To determine sensitivity of microorganisms to the antibacterial composition, 0.5 ml of broth was placed into each tube. The number of tubes was determined based on the desired number of dilutions and was increased by one for the "negative" control (no test composition). Series of two-fold serial dilutions of the test variants of the antibacterial composition were used and concentrations ranging from 450 mcg $^{64}Zn_e$/ml to 0.000107 mcg $^{64}Zn_e$/ml were obtained.

Reference test strains of S. aureus ATCC 25923, E. coli ATCC 25922 and P. aeruginosa ATCC 27853 were incubated in Mueller-Hinton liquid broth at 37° C. for 24 hours. Standard bacterial suspension equivalent to 0.5 McFarland standard diluted 100-fold with the broth was used for the inoculation of the tubes after which the concentration of microorganism in it was approximately $10^6$ CFU/ml.

0.5 ml of inoculum was added to each tube containing 0.5 ml of the appropriate dilution of a solution of the $^{64}Zn$-enriched salt of interest. 0.5 ml of inoculum also was added to one tube with 0.5 ml of broth that did not contain the $^{64}Zn$-enriched salt of interest (the "negative" control). The final concentration of the microorganism in each tube was approximately $5×10^5$ CFU/ml.

The tubes were incubated at 35° C. in air for 16-20 or 20-24 hours (depending on the bacterial strain). The tube of the negative control was placed in a refrigerator at +4° C. where it was stored till the analysis of the results.

To determine the presence of microorganism growth the test tubes with inoculum were viewed under transmitted light. Transmitted light was measured by spectrophotometry. The growth of culture in the presence of antibacterial compositions based on $^{64}Zn_e$ was compared with the reference test tube ("negative" control), containing the original inoculum and stored in the refrigerator. The MIC was determined as the lowest concentration of $^{64}Zn_e$ that inhibits visible growth of the microorganism. Both gram-positive (S. aureus) and gram-negative bacteria (P. aeruginosa, E. coli) were used in the experiments described below.

The experimental results are shown in Tables 1-5. The tables indicate the presence or absence of visible growth as a function of test culture and degree of dilution of the concentration of the antibacterial substance (zinc salt enriched for $^{64}Zn$). The salts used were citrate, EDDA, sulfate, aspartate, and glutamate.

TABLE 1

Antibacterial activity of the composition on the basis of $^{64}Zn_e$ citrate
Initial concentration of the sample: 900 mcg $^{64}Zn_e$/ml

| | Dilution No. | | | | | | | |
|---|---|---|---|---|---|---|---|---|
| | 1 | 2 | 3 | 4 | 5 | 6 | 7 | 8 |
| | | | | $\log_2$(Dilution factor)† | | | | |
| | 1 | 2 | 3 | 4 | 5 | 6 | 7 | 8 |
| | | | | Concentration of $^{64}Zn_e$, mcg/ml* | | | | |
| Test cultures | 450 | 225 | 112.5 | 56.25 | 28.13 | 14.06 | 7.03 | 3.52 |
| S. aureus | −** | − | − | − | − | − | − | − |
| E. coli | − | − | − | − | − | − | − | − |
| P. aeruginosa | − | − | − | − | − | − | + | + |

TABLE 1-continued

Antibacterial activity of the composition on the basis of $^{64}Zn_e$ citrate
Initial concentration of the sample: 900 mcg $^{64}Zn_e$/ml

| | Dilution No. | | | | | | | |
|---|---|---|---|---|---|---|---|---|
| | 9 | 10 | 11 | 12 | 13 | 14 | 15 | 16 |
| | | | | $\log_2$(Dilution factor) | | | | |
| | 9 | 10 | 11 | 12 | 13 | 14 | 15 | 16 |
| | | | | Concentration of $^{64}Zn_e$, mcg/ml | | | | |
| Test cultures | 1.76 | 0.88 | 0.44 | 0.22 | 0.11 | 0.055 | 0.027 | 0.014 |
| S. aureus | − | − | − | − | − | − | − | + |
| E. coli | − | − | − | − | − | − | − | + |
| P. aeruginosa | + | + | + | + | + | + | + | + |

| | Dilution No. | | | | | | | |
|---|---|---|---|---|---|---|---|---|
| | 17 | 18 | 19 | 20 | 21 | 22 | 23 | |
| | | | $\log_2$(Dilution factor) | | | | | |
| | 17 | 18 | 19 | 20 | 21 | 22 | 23 | |
| | | | Concentration of $^{64}Zn_e$, mcg/ml | | | | | MIC, |
| Test cultures | 0.0069 | 0.0034 | 0.0017 | 0.00086 | 0.00043 | 0.00022 | 0.00011 | mcg/ml |
| S. aureus | + | + | + | + | + | + | + | 0.0275 |
| E. coli | + | + | + | + | + | + | + | 0.0275 |
| P. aeruginosa | + | + | + | + | + | + | + | 14.062 |

†Dilution factor = $2^n$, where n is the number in the table cell. For example, where 5 is the number in the cell, the dilution factor is $2^5$ = 32: the concentration of the substance is 1/32 of the original or initial concentration.
*Non-integer substance concentrations are rounded off
**− indicates no visible growth;
"+" indicates presence of visible growth.

TABLE 2

Antibacterial activity of the composition on the basis of
$^{64}Znz$ EDDS salt ($^{64}Zn_e$ salt of ethylenediamine-N,N'-
disuccinic acid, chemical name 2-[2-[[(1)-1-carboxy-2-
carboxylatoethyl]amino]ethylamino]butanedioate)
Initial concentration of the sample: 3000 mcg $^{64}Zn_e$/ml

| | Dilution No. | | | | | | | |
|---|---|---|---|---|---|---|---|---|
| | 1 | 2 | 3 | 4 | 5 | 6 | 7 | 8 |
| | | | | $\log_2$(Dilution factor)† | | | | |
| | 1 | 2 | 3 | 4 | 5 | 6 | 7 | 8 |
| | | | | Concentration of $^{64}Zn_e$, mcg/ml* | | | | |
| Test cultures | 1500 | 750 | 375 | 187.5 | 93.75 | 46.88 | 23.44 | 11.72 |
| S. aureus | −** | − | − | − | − | − | − | − |
| E. coli | − | − | − | − | − | − | − | − |
| P. aeruginosa | − | − | − | − | − | − | − | − |

| | Dilution No. | | | | | | | |
|---|---|---|---|---|---|---|---|---|
| | 9 | 10 | 11 | 12 | 13 | 14 | 15 | 16 |
| | | | | $\log_2$(Dilution factor) | | | | |
| | 9 | 10 | 11 | 12 | 13 | 14 | 15 | 16 |
| | | | | Concentration of $^{64}Zn_e$, mcg/ml | | | | |
| Test cultures | 5.86 | 2.93 | 1.46 | 0.73 | 0.37 | 0.18 | 0.092 | 0.046 |
| S. aureus | − | − | − | − | − | ± | ± | + |
| E. coli | − | − | − | − | − | − | − | − |
| P. aeruginosa | − | − | − | + | + | + | + | + |

TABLE 2-continued

Antibacterial activity of the composition on the basis of $^{64}$Znz EDDS salt ($^{64}$Zn$_e$ salt of ethylenediamine-N,N'-disuccinic acid, chemical name 2-[2-[[(1)-1-carboxy-2-carboxylatoethyl]amino]ethylamino]butanedioate)
Initial concentration of the sample: 3000 mcg $^{64}$Zn$_e$/ml

| | Dilution No. | | | | | | | |
|---|---|---|---|---|---|---|---|---|
| | 17 | 18 | 19 | 20 | 21 | 22 | 23 | |
| | \multicolumn{7}{c}{log$_2$(Dilution factor)} | |
| | 17 | 18 | 19 | 20 | 21 | 22 | 23 | |
| | \multicolumn{7}{c}{Concentration of $^{64}$Zn$_e$, mcg/ml} | MIC, |
| Test cultures | 0.023 | 0.011 | 0.0057 | 0.0029 | 0.0014 | 0.00072 | 0.00036 | mcg/ml |
| S. aureus | + | + | + | + | + | + | + | 0.366 |
| E. coli | − | + | + | + | + | + | + | 0.0229 |
| P. aeruginosa | + | + | + | + | + | + | + | 1.465 |

†Dilution factor = $2^n$, where n is the number in the table cell. For example, where 5 is the number in the cell, the dilution factor is $2^5 = 32$: the concentration of the substance is 1/32 of the original or initial concentration.
*Non-integer substance concentrations are rounded off
**− indicates no visible growth;
"+" indicates presence of visible growth.

TABLE 3

Antibacterial activity of the composition on the basis of $^{64}$Zn$_e$ sulfate
Initial concentration of the sample: 3000 mcg $^{64}$Zn$_e$/ml

| | Dilution No. | | | | | | | |
|---|---|---|---|---|---|---|---|---|
| | 1 | 2 | 3 | 4 | 5 | 6 | 7 | 8 |
| | \multicolumn{8}{c}{log$_2$(Dilution factor)†} |
| | 1 | 2 | 3 | 4 | 5 | 6 | 7 | 8 |
| | \multicolumn{8}{c}{Concentration of $^{64}$Zn$_e$, mcg/ml*} |
| Test cultures | 1500 | 750 | 375 | 187.5 | 93.75 | 46.88 | 23.44 | 11.72 |
| S. aureus | −** | − | − | − | − | − | − | − |
| E. coli | − | − | − | − | − | − | − | − |
| P. aeruginosa | − | − | − | − | − | − | + | + |

| | Dilution No. | | | | | | | |
|---|---|---|---|---|---|---|---|---|
| | 9 | 10 | 11 | 12 | 13 | 14 | 15 | 16 |
| | \multicolumn{8}{c}{log$_2$(Dilution factor)} |
| | 9 | 10 | 11 | 12 | 13 | 14 | 15 | 16 |
| | \multicolumn{8}{c}{Concentration of $^{64}$Zn$_e$, mcg/ml} |
| Test cultures | 5.86 | 2.93 | 1.46 | 0.73 | 0.37 | 0.18 | 0.092 | 0.046 |
| S. aureus | − | − | − | − | − | ± | ± | + |
| E. coli | − | − | − | − | − | − | − | + |
| P. aeruginosa | + | + | + | + | + | + | + | + |

| | Dilution No. | | | | | | | |
|---|---|---|---|---|---|---|---|---|
| | 17 | 18 | 19 | 20 | 21 | 22 | 23 | |
| | \multicolumn{7}{c}{log$_2$(Dilution factor)} | |
| | 17 | 18 | 19 | 20 | 21 | 22 | 23 | MIC, |
| | \multicolumn{7}{c}{Concentration of $^{64}$Zn$_e$, mcg/ml} | |
| Test cultures | 0.023 | 0.011 | 0.0057 | 0.0029 | 0.0014 | 0.00072 | 0.00036 | mcg/ml |
| S. aureus | + | + | + | + | + | + | + | 0.366 |
| E. coli | + | + | + | + | + | + | + | 0.0916 |
| P. aeruginosa | + | + | + | + | + | + | + | 46.875 |

†Dilution factor = $2^n$, where n is the number in the table cell. For example, where 5 is the number in the cell, the dilution factor is $2^5 = 32$: the concentration of the substance is 1/32 of the original or initial concentration.
*Non-integer substance concentrations are rounded off
**− indicates no visible growth;
"+" indicates presence of visible growth.

TABLE 4

Antibacterial activity of the composition on the basis of $^{64}Zn_e$ aspartate
Initial concentration of the sample: 1500 mcg/ml

| | Dilution No. | | | | | | | |
|---|---|---|---|---|---|---|---|---|
| | 1 | 2 | 3 | 4 | 5 | 6 | 7 | 8 |
| | | | | $\log_2$(Dilution factor)† | | | | |
| | 1 | 2 | 3 | 4 | 5 | 6 | 7 | 8 |
| | | | | Concentration of $^{64}Zn_e$, mcg/ml* | | | | |
| Test cultures | 750 | 375 | 187.5 | 93.75 | 46.88 | 23.44 | 11.72 | 5.86 |
| S. aureus | –** | – | – | – | – | – | – | – |
| E. coli | – | – | – | – | – | – | – | – |
| P. aeruginosa | – | – | – | – | – | – | – | – |

| | Dilution No. | | | | | | | |
|---|---|---|---|---|---|---|---|---|
| | 9 | 10 | 11 | 12 | 13 | 14 | 15 | 16 |
| | | | | $\log_2$(Dilution factor) | | | | |
| | 9 | 10 | 11 | 12 | 13 | 14 | 15 | 16 |
| | | | | Concentration of $^{64}Zn_e$, mcg/ml | | | | |
| Test cultures | 2.93 | 1.46 | 0.73 | 0.37 | 0.18 | 0.092 | 0.046 | 0.023 |
| S. aureus | – | – | – | – | – | – | – | – |
| E. coli | – | – | – | – | – | – | – | – |
| P. aeruginosa | – | – | – | + | + | + | + | + |

| | Dilution No. | | | | | | | |
|---|---|---|---|---|---|---|---|---|
| | 17 | 18 | 19 | 20 | 21 | 22 | 23 | |
| | | | | $\log_2$(Dilution factor) | | | | |
| | 17 | 18 | 19 | 20 | 21 | 22 | 23 | |
| | | | | Concentration of $^{64}Zn_e$, mcg/ml | | | | MIC, |
| Test cultures | 0.011 | 0.0057 | 0.0029 | 0.0014 | 0.00072 | 0.00036 | 0.00018 | mcg/ml |
| S. aureus | – | – | + | + | + | + | + | 0.0057 |
| E. coli | + | + | + | + | + | + | + | 0.0229 |
| P. aeruginosa | + | + | + | + | + | + | + | 0.732 |

†Dilution factor = $2^n$, where n is the number in the table cell. For example, where 5 is the number in the cell, the dilution factor is $2^5$ = 32: the concentration of the substance is 1/32 of the original or initial concentration.
*Non-integer substance concentrations are rounded off
**– indicates no visible growth;
"+" indicates presence of visible growth.

TABLE 5

Antibacterial activity of the composition on the basis of $^{64}Zn_e$ glutamate
Initial concentration of the sample: 1500 mcg/ml

| | Dilution No. | | | | | | | |
|---|---|---|---|---|---|---|---|---|
| | 1 | 2 | 3 | 4 | 5 | 6 | 7 | 8 |
| | | | | $\log_2$(Dilution factor)† | | | | |
| | 1 | 2 | 3 | 4 | 5 | 6 | 7 | 8 |
| | | | | Concentration of $^{64}Zn_e$, mcg/ml* | | | | |
| Test cultures | 750 | 375 | 187.5 | 93.75 | 46.88 | 23.44 | 11.72 | 5.86 |
| S. aureus | –** | – | – | – | – | – | – | – |
| E. coli | – | – | – | – | – | – | – | – |
| P. aeruginosa | – | – | – | – | – | – | – | – |

TABLE 5-continued

Antibacterial activity of the composition on the basis of $^{64}Zn_e$ glutamate
Initial concentration of the sample: 1500 mcg/ml

|  | Dilution No. | | | | | | | |
|---|---|---|---|---|---|---|---|---|
|  | 9 | 10 | 11 | 12 | 13 | 14 | 15 | 16 |
|  | | | | log$_2$(Dilution factor) | | | | |
|  | 9 | 10 | 11 | 12 | 13 | 14 | 15 | 16 |
|  | | | | Concentration of $^{64}Zn_e$, mcg/ml | | | | |
| Test cultures | 2.93 | 1.46 | 0.73 | 0.37 | 0.18 | 0.092 | 0.046 | 0.023 |
| S. aureus | − | − | − | − | − | − | − | + |
| E. coli | − | − | − | − | − | − | − | − |
| P. aeruginosa | − | − | − | − | − | + | + | + |

|  | Dilution No. | | | | | | |  |
|---|---|---|---|---|---|---|---|---|
|  | 17 | 18 | 19 | 20 | 21 | 22 | 23 |  |
|  | | | log$_2$(Dilution factor) | | | | |  |
|  | 17 | 18 | 19 | 20 | 21 | 22 | 23 |  |
|  | | | Concentration of $^{64}Zn_e$, mcg/ml | | | | | MIC, |
| Test cultures | 0.011 | 0.0057 | 0.0029 | 0.0014 | 0.00072 | 0.00036 | 0.00018 | mcg/ml |
| S. aureus | + | + | + | + | + | + | + | 0.0458 |
| E. coli | − | − | + | + | + | + | + | 0.0057 |
| P. aeruginosa | + | + | + | + | + | + | + | 0.183 |

†Dilution factor = $2^n$, where n is the number in the table cell. For example, where 5 is the number in the cell, the dilution factor is $2^5$ = 32: the concentration of the substance is 1/32 of the original or initial concentration.
*Non-integer substance concentrations are rounded off
**− indicates no visible growth;
"+" indicates presence of visible growth.

To evaluate the bactericidal action of the antibacterial composition based on light isotope $^{64}Zn_e$ the minimum bactericidal concentration (MBC) was determined by plating out 0.1 ml of the contents of each tube containing the antibacterial composition on Mueller-Hinton medium. The incubation was at 37° C. for 24 h.

The MBC of the test samples was determined as the lowest concentration at which there was no growth on Mueller-Hinton agar medium. The established MBC values are given in Table 6.

TABLE 6

The MBC for all samples of the antibacterial composition based on light isotope $^{64}Zn_e$ for test cultures
MBC, mcg $^{64}Zn_e$/ml

| Test culture | $^{64}Zn_e$ citrate | $^{64}Zn_e$ EDDS | $^{64}Zn_e$ sulfate | $^{64}Zn_e$ asparaginate | $^{64}Zn_e$ glutamate |
|---|---|---|---|---|---|
| S. aureus | 0.028* | 0.73* | 0.37* | 0.023* | 0.046* |
| E. coli | 0.44* | 2.93* | 1.46* | 0.73* | 0.37* |
| P. aeruginosa | 112.5 | 375 | 375 | >750 | >750 |

*Value is rounded off.

Figure 2C:
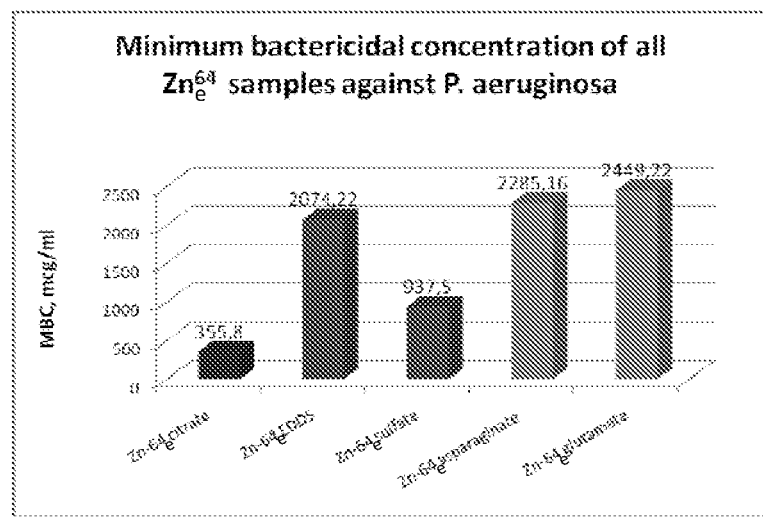
FIG. 2 presents diagrams (FIGS. 2a-2c) that compare the MBCs of antibacterial compositions that contain zinc enriched for $^{64}$Zn in the form of different salts: $^{64}$Zn$_e$ citrate, $^{64}$Zn$_e$ EDDA, $^{64}$Zn$_e$ sulfate, $^{64}$Zn$_e$ aspartate, $^{64}$Zn$_e$ glutamate.

The data presented above show that the antibacterial composition of the invention had a pronounced bacteriostatic (Tables 1-5) and bactericidal activity (Table 6). All samples of the composition demonstrated good indicators of bacteriostatic activity against S. aureus and E. coli. As for P. aeruginosa, the best results were recorded for the antibacterial composition which included $^{64}Zn_e$ in the form of salt with EDDA, aspartic acid and glutamic acid (see FIG. 1). Bactericidal activity of the antibacterial composition against S. aureus and E. coli was sufficiently high in all the samples. The samples of the antibacterial composition based on $^{64}Zn_e$ in the form of citrate, sulfate and salt with EDDA (see FIG. 2) showed satisfactory bactericidal activity against P. aeruginosa.

Figure 3C:
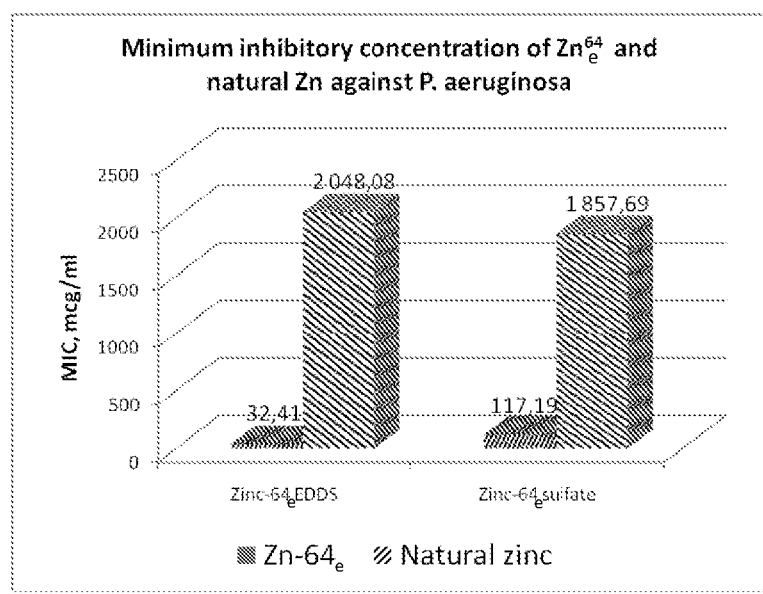
FIG. 3 presents diagrams (FIGS. 3a-3c) that compare the MIC of antibacterial compositions of the invention that contain zinc enriched for $^{64}$Zn in the form of the EDDA and sulfate salts to compositions that contain naturally-occurring zinc (not enriched for $^{64}$Zn).
Figures 4, 4A:
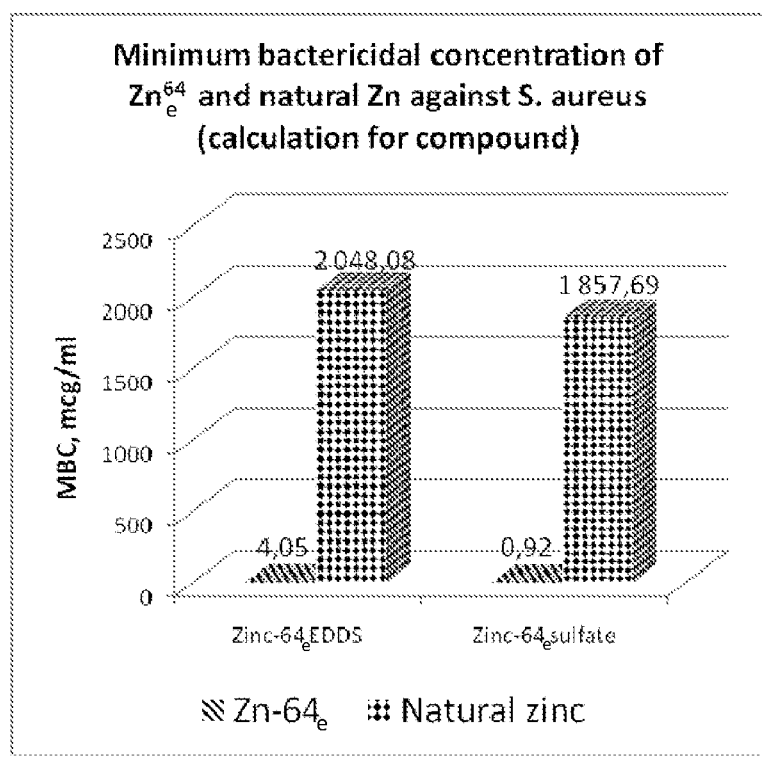
FIG. 4 presents diagrams (FIGS. 4a-4c) that compare the MBC of antibacterial compositions of the invention that contain zinc enriched for $^{64}$Zn in the form of the EDDA and sulfate salts to compositions that contain naturally-occurring zinc (not enriched for $^{64}$Zn).
Figure 4B:
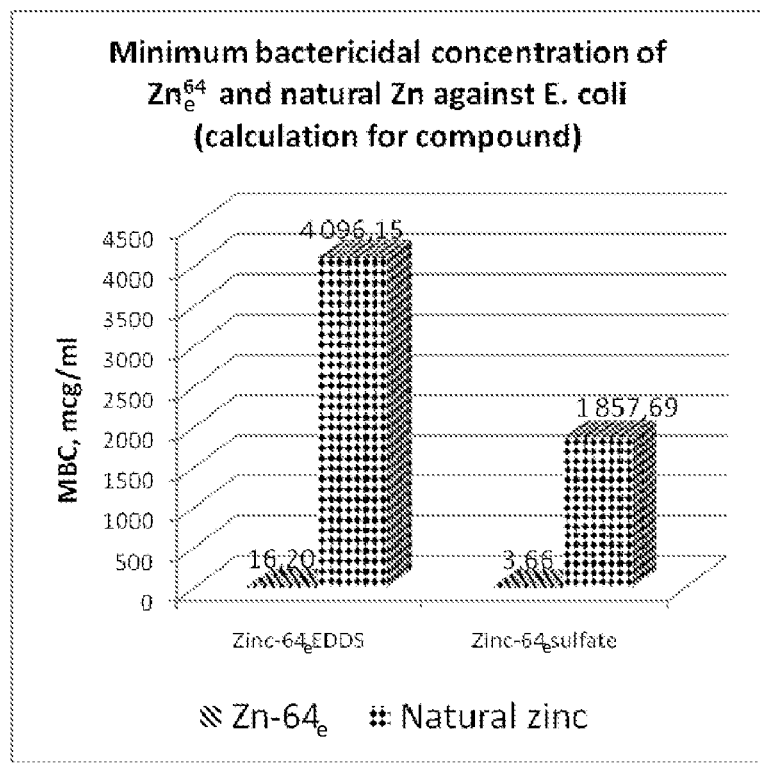
Figure 4C:
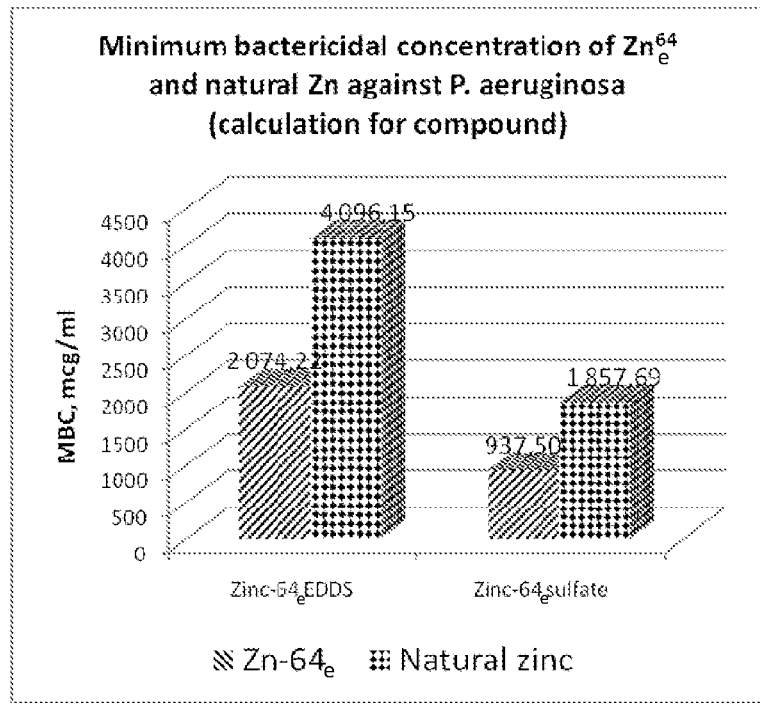

Example 3. Comparison of Properties of the Antibacterial Composition with a Zinc-Based Composition with Natural Distribution of Isotopes For further studies of the antibacterial properties of a composition in accordance with the invention to confirm the fact that its bacteriostatic and bactericidal activities are due to the enrichment of the light isotope $^{64}Zn$ in the composition, a parallel experiment was carried out to compare the antibacterial properties of a composition that includes zinc that is not enriched for $^{64}Zn$. That is, $^{64}Zn_e$ in the form of a salt was compared with a composition that contains zinc with a natural distribution of isotopes. The conditions of the experiment were the same as those described in Example 1. The antibacterial composition of the invention containing $^{64}Zn_e$ in the form of a salt with EDDA and in the form of $^{64}Zn_e$ sulfate served as the samples for the comparison. Relevant samples containing salt of natural zinc with EDDA and natural zinc sulfate were used for the comparison. The findings of the study of the bacteriostatic activity (MIC values) are shown in Table 7 and FIG. 3; the findings of the study of the bactericidal activity (MBC values) are shown in Table 8 and FIG. 4.

TABLE 7

Comparative figures of MIC of samples containing
$^{64}Zn_e$ and samples with natural zinc
MIC, zinc/ml

| Test culture | $^{64}Zn_e$ EDDS | Natural zinc - EDDS | $^{64}Zn_e$ sulfate | Natural zinc - sulfate |
|---|---|---|---|---|
| S. aureus | 0.73 | 93.75 | 0.366 | 93.75 |
| E. coli | 0.18 | 375 | 0.0916 | 187.5 |
| P. aeruginosa | 5.86 | 375 | 46.875 | 750 |

TABLE 8

Comparative figures of MBC of samples containing
$^{64}Zn_e$ and samples with natural zinc
MBC, mcg zinc/ml

| Test culture | $^{64}Zn_e$ EDDS | Natural zinc as part of EDDS | $^{64}Zn_e$ sulfate | Natural zinc sulfate |
|---|---|---|---|---|
| S. aureus | 0.7324 | 375 | 0.3662 | >750 |
| E. coli | 2.9296 | >750 | 1.4648 | >750 |
| P. aeruginosa | 375 | >750 | 375 | >750 |

The data above show that the antibacterial composition of the invention containing $^{64}Zn$-enriched zinc demonstrated a bacteriostatic activity which is significantly higher than that of the zinc-based preparations with the natural isotope distribution (by a factor of about 15 to about 2000 maximum). The bactericidal activity of the composition of the invention in all cases was significantly higher than that of the preparation containing natural zinc in the form of similar salt. Thus it was confirmed that the bacteriostatic and bactericidal activities of the antibacterial composition of the invention is directly attributable to the presence of light isotope $^{64}Zn$-enriched zinc in the form of a salt of an organic or inorganic acid.

Example 4

Figure 5C:
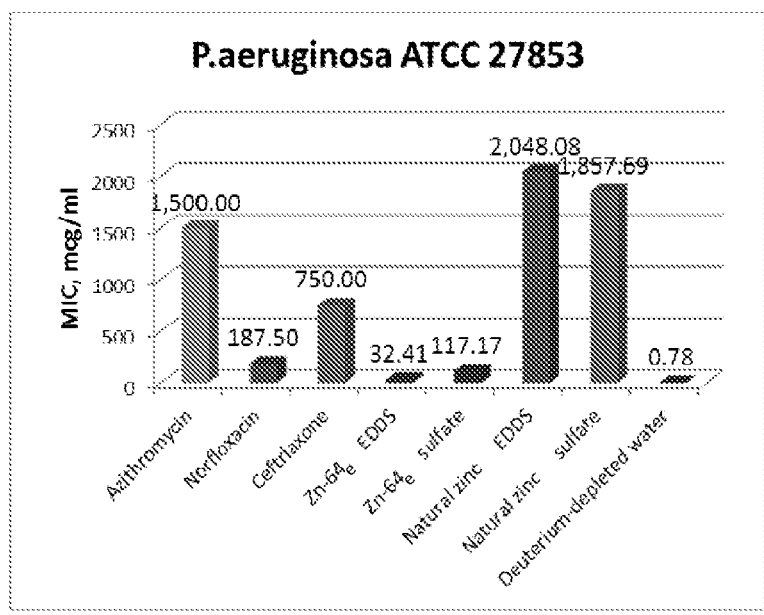
FIG. 5 presents diagrams (FIGS. 5a-5c) that compare antibacterial compositions of the invention that contain zinc enriched for $^{64}$Zn in the form of different salts to compositions that contain naturally-occurring zinc (not enriched for $^{64}$Zn) and to known antibacterial agents.

To confirm the effectiveness of the antibacterial composition of the present invention, a parallel experiment was carried out for its comparison with known antibacterial agents. The following commercial antibacterial medications were used for the study: azithromycin and ceftriaxone and norfloxacin. The initial concentration of 3000 mcg/ml was used for the samples of all the above compounds. The conditions of the experiment were similar to those described in Example 1. Serial dilutions of the above antibacterial compounds were also prepared in the same way as for the antibacterial composition of the invention. The same pathogenic strains of S. aureus ATCC 25923, E. coli ATCC 25922, P. aeruginosa ATCC 27853 were used for the study. The MIC and MBC established for the antibacterial agents are shown in Tables 9 and 10, respectively. The comparison of bactericidal and bacteriostatic activities of the antibacterial composition of the present invention and commercial antibacterial agents is shown in diagrams in FIG. 5.

TABLE 9

MIC of azithromycin, norfloxacin and
ceftriaxone against test strains

| Test cultures | MIC, mcg/ml azithromycin | MIC, mcg/ml norfloxacin | MIC, mcg/ml ceftriaxone |
|---|---|---|---|
| S. aureus ATCC 25923 | 187.5 | 11.72* | 11.72* |
| E. coli ATCC 25922 | 1500 | 23.44* | 2.93* |
| P. aeruginosa ATCC 27853 | 1500 | 187.5 | 750 |

*Value is rounded off to the nearest 0.01.

TABLE 10

MBC of azithromycin, norfloxacin and
ceftriaxone against test strains

| Test cultures | MBC, mcg/ml azithromycin | MBC, mcg/ml norfloxacin | MBC, mcg/ml ceftriaxone |
|---|---|---|---|
| S. aureus ATCC 25923 | <1500 | <1500 | 375 |
| E. coli ATCC 25922 | <1500 | <1500 | 11.72* |
| P. aeruginosa ATCC 27853 | <1500 | <1500 | <1500 |

*Value is rounded off to the nearest 0.01.

As seen from the above data, the MIC and MBC of the commercial antibacterial agents are much inferior to those of the antibacterial composition of the invention which confirms its efficiency and expediency of application for the control of pathogenic microorganisms.

Example 5

Determination of the Minimum Inhibitory Concentration of Deuterium-Depleted Water The minimum inhibitory concentration (MIC) of deuterium-depleted water was determined by serial dilutions in normal saline solution. Reference strains of E. coli ATCC 25922 and P. aeruginosa ATCC 27859 were used as test cultures. For inoculation, microbial suspension equivalent to a 0.5 standard McFarland ($1.5 \times 10^8$ cells/ml) was used. Then the dilutions with normal saline solution were prepared so that the concentration of microorganisms reached approximately $10^4$ cells/ml. The test cultures were previously grown for 24 hours at 37° C. One-tenth of a milliliter (0.1 ml) of the suspension was placed into each test tube containing 4 ml of the medium with the investigative active substance at a certain concentration (without deuterium-depleted water in the control). The tubes were incubated in an incubator at 37° C. for 24 hours. After incubation the inoculum from each tube was plated on Mueller-Hinton agar medium for P. aeruginosa and on Endo for E. coli and incubated at 37° C. for another 24 hours. The results were evaluated based on the presence of bacterial growth (turbidity) in the nutrient broth and, if necessary, by using other additional known bacteriological tests. The first few tubes remained transparent due to the antimicrobial effect of the study substance. The emergence of growth in the other tubes suggests that the drug concentration was below the minimum bactericidal concentration, which is determined by the last test tube in a series which had no signs of microbial growth. The results are shown in the table below and illustrated in FIGS. 5b and 5c.

TABLE 11

Antibacterial activity of deuterium-depleted water in the experiments of Example 5

| Strain of micro-organism | Volume of study substance in a tube is 1 ml Dilution of study substance: | | | | | | | | | |
|---|---|---|---|---|---|---|---|---|---|---|
| | 1:5 | 1:10 | 1:20 | 1:40 | 1:80 | 1:160 | 1:320 | 1:640 | 1:1280 | 1:2560 |
| E. coli ATCC 25922 | − | − | − | − | − | − | − | − | − | + |
| P. aeruginosa ATCC 27859 | − | − | − | − | − | − | − | − | − | + |

Findings

The basic solution of deuterium-depleted water without adding the study drugs had a bactericidal effect on P. aeruginosa ATCC 27853 and E. coli ATCC 25922 at concentrations of $10^4$, $10^6$, $10^8$ cells/ml.

Pure deuterium-depleted water is the best disinfectant for E. coli ATCC 25922 and P. aeruginosa ATCC 27853 bacteria.

The MIC of deuterium-depleted water for P. aeruginosa ATCC and E. coli is its 1:1280 dilution.

What is claimed is:

1. A method of treating a condition that is caused by or characterized by a bacterial infection or excessive bacterial growth, wherein the method comprises administering an antibacterial composition comprising a bacteriostatic or bactericidal effective amount of at least one light isotope-enriched element selected from the group consisting of Si that is at least 95% $^{28}$Si; K that is at least 98% $^{39}$K; Mg that is at least 95 $^{24}$Mg, Rb that is at least 90% $^{85}$Rb; Mo that is at least 80% $^{92}$Mo; Se that is at least 50% $^{74}$Se; Ge that is at least 90% $^{70}$Ge; Cr that is at least 90% $^{52}$Cr; Fe that is at least 80% $^{54}$Fe; Ni that is at least 90% $^{58}$Ni; Cu that is at least 90% $^{63}$Cu; and V that is at least 35% 50V, wherein the light isotope-enriched element is present in elemental form or in the form of a pharmaceutically acceptable salt, compound or complex thereof, to said person or said veterinary mammal.

2. The method of claim 1, wherein the condition is acne.

3. The method of claim 1, wherein the condition is sepsis.

4. The method of claim 1, wherein the condition is a bacterial infection.

* * * * *